(12) United States Patent
Waggoner et al.

(10) Patent No.: US 6,479,303 B1
(45) Date of Patent: *Nov. 12, 2002

(54) FLUORESCENT LABELING COMPLEXES WITH LARGE STOKES SHIFT FORMED BY COUPLING TOGETHER CYANINE AND OTHER FLUOROCHROMES CAPABLE OF RESONANCE ENERGY TRANSFER

(75) Inventors: Alan S. Waggoner, Pittsburgh, PA (US); Swati R. Mujumdar, Glenshaw, PA (US); Ratnakar B. Mujumdar, Glenshaw, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/151,899

(22) Filed: Sep. 11, 1998

Related U.S. Application Data

(62) Division of application No. 08/476,880, filed on Jun. 7, 1995, now Pat. No. 6,008,373.

(51) Int. Cl.⁷ .................. G01N 33/533; G01N 33/546; G01N 33/548; G01N 33/552; G01N 33/554
(52) U.S. Cl. ..................... 436/546; 435/6; 435/7.2; 435/188; 436/527; 436/529; 436/530; 436/534; 436/800; 530/391.3; 530/391.5; 530/402; 530/409
(58) Field of Search .................. 530/391.3, 391.5, 530/402, 409; 436/546, 534, 527, 529, 800, 530; 435/188, 6, 7.2

(56) References Cited

U.S. PATENT DOCUMENTS

| | | | |
|---|---|---|---|
| 4,745,285 A | 5/1988 | Recktenwald et al. | |
| 4,774,339 A | 9/1988 | Haugland et al. | 548/405 |
| 4,777,128 A | 10/1988 | Lippa | |
| 4,876,190 A | 10/1989 | Recktenwald et al. | 436/513 |
| 4,900,686 A | 2/1990 | Arnost et al. | 436/546 |
| 4,996,143 A | 2/1991 | Heller et al. | |
| 5,118,802 A | 6/1992 | Smith et al. | |
| 5,248,782 A | 9/1993 | Haugland et al. | 548/405 |
| 5,254,477 A | 10/1993 | Walt | |
| 5,268,486 A | 12/1993 | Waggoner et al. | 548/427 |
| 5,274,113 A | 12/1993 | Kang et al. | |
| 5,326,692 A | 7/1994 | Brinkley et al. | |
| 5,332,662 A | 7/1994 | Ullman | 435/28 |
| 5,342,789 A | 8/1994 | Chick et al. | |
| 5,378,634 A | 1/1995 | Nobuyuki et al. | 436/91 |
| 5,401,847 A | 3/1995 | Glazer et al. | |
| 5,410,030 A | 4/1995 | Yue et al. | 536/23.1 |
| 5,439,797 A | 8/1995 | Tsien et al. | |
| 5,453,505 A | 9/1995 | Lee et al. | 544/124 |
| 5,532,129 A | 7/1996 | Heller | |
| 5,552,540 A | 9/1996 | Haralambidis | |
| 5,565,322 A | 10/1996 | Heller | |
| 5,565,554 A * | 10/1996 | Glazer et al. | 536/26.6 |
| 5,573,909 A | 11/1996 | Singer et al. | |
| 5,582,977 A | 12/1996 | Yue et al. | |
| 5,646,264 A | 7/1997 | Glazer et al. | |
| 5,654,419 A | 8/1997 | Mathies et al. | 536/25.4 |
| 5,688,648 A | 11/1997 | Mathies et al. | |
| 5,707,804 A | 1/1998 | Mathies et al. | |
| 5,760,201 A | 6/1998 | Glazer et al. | |
| 5,763,189 A * | 6/1998 | Buechler et al. | 435/7.1 |
| 5,824,799 A * | 10/1998 | Buechler et al. | 540/128 |
| 5,843,658 A | 12/1998 | Uchiyama et al. | |
| 5,851,778 A | 12/1998 | Oh et al. | |
| 5,869,255 A | 2/1999 | Mathies et al. | |
| 6,008,373 A * | 12/1999 | Waggoner et al. | |
| 6,028,190 A | 2/2000 | Mathies et al. | |
| 6,048,982 A | 4/2000 | Waggoner | |

FOREIGN PATENT DOCUMENTS

| | | |
|---|---|---|
| EP | 0 428 000 A1 | 5/1991 |
| EP | 0 601 889 A2 | 6/1994 |
| EP | 0 609 894 A | 8/1994 |
| EP | 0 710 668 A | 5/1996 |
| GB | 2 301 833 B | 12/1996 |
| JP | 05060698 | 12/1993 |
| WO | 87/07385 | 12/1987 |
| WO | 88/04777 | 6/1988 |
| WO | WO 89/03041 A2 | 4/1989 |
| WO | 0229943 B1 | 9/1991 |
| WO | 91/16336 | 10/1991 |
| WO | WO 92/00388 A1 | 1/1992 |
| WO | 93 06482 | 4/1993 |
| WO | WO 93/09128 A1 | 5/1993 |

(List continued on next page.)

OTHER PUBLICATIONS

P.R. Slevin, "Fluorescence Resonance Energy Transfer" *Methods In Enzymol.* 1995, 246, 300–334.

(List continued on next page.)

Primary Examiner—Mary E. Ceperley
(74) Attorney, Agent, or Firm—Kirkpatrick & Lockhart LLP

(57) ABSTRACT

The present invention provides low molecular weight fluorescent labeling complexes with large wavelength shifts between absorption of one dye in the complex and emission from another dye in the complex. These complexes can be used, for example, for multiparameter fluorescence cell analysis using a single excitation wavelength. The low molecular weight of the complex permits materials labeled with the complex to penetrate cell structures for use as probes. The labeling complexes are synthesized by covalently attaching through linkers at least one cyanine fluorochrome to another low molecular weight fluorochrome to form energy donor-acceptor complexes. Resonance energy transfer from an excited donor to fluorescent acceptor provides wavelength shifts up to 300 nm. The fluorescent labeling complexes preferably contain reactive groups for the labeling of functional groups on target compounds, such as derivatized oxy and deoxy polynucleic acids, antibodies, enzymes, proteins and other materials. The complexes may also contain functional groups permitting covalent reaction with materials containing reactive groups.

29 Claims, 10 Drawing Sheets

FOREIGN PATENT DOCUMENTS

| WO | WO 93/23492 A1 | 11/1993 |
|---|---|---|
| WO | WO 94/06812 A1 | 3/1994 |
| WO | WO 94/17397 A1 | 8/1994 |
| WO | 94 24213 | 10/1994 |
| WO | WO 94/28166 A1 | 12/1994 |
| WO | 95/08772 | 3/1995 |
| WO | 96/04405 A1 | 2/1996 |
| WO | 96/29367 | 9/1996 |
| WO | WO 96/41166 A2 | 12/1996 |

OTHER PUBLICATIONS

S. C. Bensen, et al., "Heterodimeric DNA–binding dyes designed for energy transfer: stability and applications of the DNA complexes." *Nucleic Acids Res.* 1993, 21, 5720–5726.

S.C. Bensen, et al., "Heterodimeric DNA–Binding dyes designed for energy transfer: synthesis and spectroscopic Properties." *Nucleic Acids Res.* 1993, 21, 5727–5735.

J. L. Mergeny, et al., "Fluorescence energy transfer as a probe for nucleic acid structures and sequences." *Nucleic Acids Res.* 1994, 22, 920–928.

B. Valeur, et al., "Calculation of the distribution of donor–acceptor distances in flexible bichromophoric molecules. Application to intramolecular transfer of excitation energy" *J. Phys. Chem.* 1989, 93, 6073–6079.

H. Ozaki and L. W. McLaughlin, "Fluorescence resonance energy transfer between specific–labeled sites on DNA", *Nucleic Acids Symposium Series* 1992, 27, 67–68.

H. Ozaki and L. W. McLaughlin, "The estimation of distances between specific backbone–labeled sites in DNA using fluorescence resonance energy transfer"*Nucleic Acids Res.* 1992, 20, 5205–5214.

K. G. Rice, et al., "Interterminal distance and flexibility of a triantennary glycopeptide as measured by resonance energy transfer." *Biochemistry* 1991, 30, 6646–6655.

J. A. Anton, et al., "Transfer of excitation energy between porphyrin centers of a covalently linked dimer." *Photochem. Photobiol.* 1978, 28, 235–242.

G. D. Scholes, et al., "Intramolecular electronic energy transfer between rigidly linked naphthalene and anthracene chromophores" *J. Phys. Chem.* 1993, 97, 11871–11876.

A. M. Oliver, et al., "Strong effects of the bridge configuration on photoinduced charge separation in rigidly linked donor–acceptor systems" *Chem. Phys. Lett.* 1988, 150, 366–373.

T. Scherer, "Comparison of flexibly and rigidly bridged donor–acceptor systems: solvent induced switching between folded and extended emissive charge–transfer states" *Rec. Trav. Chim. Pays–Bas.* 1991, 110, 95–96.

W. Yingshen & K. S. Schanze, "Photochemical probes of intramolecular electron and energy transfer" *Chem. Phys.* 1993, 176, 305–319.

H. E. Katz, & W. T. Lavell, "4–Piperidinylimino : a nearly linear head–to–tail linking group for dipolar chromophores" *J. Org. Chem.* 1991, 56, 2282–2284.

P. Yuan, "Photophysical Behavior of bichromophores and energy transfer–based indicators" Ph.D. Dissertation, 1991, Tufts University.

J. Yang & M. A. Winnik, "Fluorescence energy transfer studies in a cross–linked polyurethane network" *Can. J. Chem.* 1995, 73, 1823–1830.

H. Tian, et al., "Bichromophoric Rhodamine Dyes and Their Fluorescence Properties" *Dyes and Pigm.* 1994, 26, 159–165.

B. Pispisa, et al., "Photophysical behavior of Poly(L–lysine) carrying Prophyrin and Naphthyl Chromophors" *Biopolymers,* 1994, 34 435–442.

M. Sauer, et al., "Design of Multiplex Dyes" *Ber. Bunsenges Phys. Chem.* 1993, 97, 1734–1737.

M. J. Lerho, "Diffusion –enhanced fluorescence energy transfer (DEFET): Application to the study of ligands—DNA and –chromatin interaction" PhD Dissertation 1991: Universite de l'etat a Liege (Belgium).

T. K. Hirzel, "Singlet excitation transfer between terminal chromophores in 1,4–disubstituted bicyclo (2.2.2) octanes and 4,4'–disubstituted–1.1'–dibicyclo (2.2.2) octyls" Ph.D. Dissertation, 1980, University of Wisconsin–Madison.

R. Nakagaki, et al., "Photochemistry of bichromophoric chain molecule containing electron donor and acceptor moieties. Dependence of reaction pathways on the chain length and mechanism of photoredox raction of N–(ω–(p–nitrophenoxy)alkyl)anilines" *Chem. Phys. Lett.* 1985, 121, 262–266.

U. Asseline, et al., "Oligodeoxynucleotides Covalently Linked to Intercalating Dyes as Base Sequence–Specific Ligands; Influence of Dye Attachment Site" *EMBO Journal* 1984, 3, 795–800.

D. Bergstrom, et al., "C–5–Substituted Nucleoside Analogs" *Synlett* 1992, 3, 179–188.

J. Brumbaugh, et al., "Continuous, On–line DNA Sequencing Using Oligodeoxynucleotide Primers with Multiple Fluorophores" *Proc. Natl. Acad. Sci.* USA 1988, 85, 5610–5614.

R. A Cardullo, et al., "Detection of Nucleic acid hybridization by nonradiative fluorescence resonance energy transfer" *Proc. Natl. Acad. Sci.* USA 1988, 85, 8790–8794.

R. M. Clegg, "Fluorescence Resonance energy transfer and nucleic acids" *Methods In Enzymol.* 1992, 211, 353–389.

J. P. Cooper & P. J. Hagerman, "Analysis of Fluorescence Energy Transfer in Duplex and Branched DNA Molecules" *Biochemistry* 1990, 29, 9261–9268.

J. M. Drake, et al., "Chemical and Biological Microstructures as probed by dynamic processes" *Science,* 1991, 251, 1574–1579.

R. P. Haugland, "Synthesis and Biomedical Applications of Fluorescent Probes" Small Business Innovative Research Program, Phase I Grant Application, submitted Dec. 13, 1985.

R. P. Haugland, "Synthesis and Applications of Fluorescent Probes" Small Business Innovative Research Program, Phase II Grant Application.

M. J. Heller, et al. "Fluorescent Energy Transfer Oligonucleotide Probes" *Federation Proceedings* 1987, 46(6) Abstract 248.

R.P. Haugland, et al., "Dependence of the kinetics of singlet–singlet energy transfer on spectral overlap" *Natl. Acad. Sci.* 1969, 63, 23–30.

L. G. Lee, et al., "Allelic discrimination by nick–translation PCR with fluorogenic probes" *Nucleic Acids Res.* 1993, 21, 3761–3766.

F. P. Schaefer, et al., "Intramolecular TT–energy transfer in bifluorophoric laser dyes" *Appl. Phys. B,* 1982, B28(1) 37–41.

K. J. Livak, et al., "Oligonucleotides with fluorescent dyes at opposite ends proved a quenched probe system useful for detecting PCR product and nucleic acid hybridization" *PCR Methods Appl.* 1995, 4, 357–362.

M. T. Shipchandler, et al., "4'-[Aminomethyl]fluorescein and its N–alkyl derivatives: useful reagents in immunodiagonostic techniques" *Anal. Biochem.* 1987, 162, 89–101.

R. Stenzel, et al., "Cross–reactivity of Anti–Digoxin Antibodies with Digotoxin Depends on Tracer Structure" *Clin. Chem.* 1992, 38, 2228–2232.

P. Wu "Resonance energy transfer: methods and applications" *Anal. Biochem.* 1994, 218, 1–13.

H. Tian & K. Chen, "Solvent effect on the triplet lifetime of some rhodamine dyes" *Dyes. Pigm.* 1994, 26, 167–174.

M. S. A. Abdel–Mottaleb, et al., "Photophysics and dynamics of coumarin laser dyes and their analytical implications" *Proc.—Indian Acad. Sci. Chem. Sci.* 1992, 104, 185–195.

R. P. Haugland, "Fluorescent Labels" *Biosense. Fiberopt.* 1991, 85–110.

S. A. Latt, et al., "Energy Transfer. A system with relatively fixed Donor–acceptor Separation" J. Am. Chem. Soc. 1965, 87, 995–1003.

T. Förster. "Intermolecular energy migration and fluorescence" *Ann. Physik (Leipzig)* 1948, 2, 55.

T. Forster, "Mechanism of Energy Transfer", Laboratory for Physical Chemistry, Technical University, Stuttgart (German) pp. 61–77.

F. P. Schaefer, "B–fluorophooric Laser Dyes With Intramolecular Energy Transfer", *Chem. Phys. Lett.* 1978, 56, 455.

R. P. Haugland, et al., New Dyes for DNA Sequencing (Progress report).

D. P. Millar, et al., "Excited–state quenching of dye–linked oligonucleotides" *Proc. SPIE–Int. Soc. Opt. Eng.* 1992, 1640, 592–598.

R. P. Haugland, "Molecular Probes Handbook of Fluorescent Probes and Research Chemical" 1992–1994 5th Ed., Molecular Probes, Inc.

H. C. Chiu & R. Bersohn, "Electronic energy transfer between tyrosine and tryptophan in the peptides Tyr–(Pro)n–Tye," *Biopolymers* (1977), 16, 277.

R. H. Conrad & L. Brand, "Intermolecular transfer of excitation from tryptophan to 1–dimethylaminonaphthalene–5–sulfonamide in a series of model compounds." *Biochemistry,* 1968, 7, 5777.

E. Hass, et al., "Distribution of end–to–end distances in oligopeptides in solution as estimated by energy transfer" *Proc. Natl. Acad. Sci* USA 1975, 72, 1807.

A. A. Lamola, et al., "Intramolecular energy transfer between nonconjugated chromophores in some model compounds" *J. Am. Chem. Soc.* 1965, 37, 2322.

J. Mugnier, et al., "Efficiency of intramolecular energy transfer in coumarin bichromophoric molecules" *Lumin.* 1985, 33, 273.

J. Mugnier, et al., "Rate of intramolecular electronic energy transfer in coumarin bichromphoric molecules. An investigation by multifrequency phase–modulation fluorometry" *Chem. Phys. Lett.* 1985, 119, 217.

O. Schnepp & M. J. Levy, "Intramolecular energy transfer in a naphthalene–anthracene system" *J. Am. Chem. Soc.* 1962, 84, 172.

T. Tamaki, "Intermolecular interaction between the phenol and indole chromophore" *Bull Soc. Chem. Jap.* 1973, 46, 2526.

G. Weber, et al., Fluorescence exciation spectrum of organic compounds in solution Part I. Systems with quantum yield independent of exciting wavelength. *Trans. Faraday Soc.* 1958, 54, 640.

S. Speiser & J. Katriel, "Intramolecular electronic energy transfer via exchange interaction in bichromophoric molecules" *Chem. Phys. Lett.,* 1983, 102, 88–94.

Hee–Chol Kang, et al., "New Dyes for DNA sequencing" *Human Genome* 1989–90, Program Report (U.S. Department of Energy, Office of Energy Research).

J. Ju, et al., "Fluorescent energy transfer dye–labeled primers for DNA sequencing and analysis" University of California, Berkeley, Jan. 1995, 4347–4350.

Haugland, Richard P., "Fluorescence–Detected DNA Sequencing, Final Technical Report" for the period from Sep. 30, 1988–Sep. 29, 1990, research Grant No. DE–FG06–88ER60684.

A. I. Kiprianov and G. G. Dyadyusha Absorption Spectra of Organic Dyes Containing Two Conjugated Chromophores in the Molecule, Ukrainskii Khimicheskii Zhurnal, vol. 35, No. 6, pp. 608–615, 1969.

Lubert Stryer and Richard P. Haugland Energy Transfer: A spectroscopic Ruler, Proc. N.A.S., vol. 58, pp. 719–726, 1967.

Ratnakar B. Mujumdar et al. Cyanine Dye Labeling Reagents: Sulfoindocyanine Succinimidyl Esters, Bioconjugate Chem., vol. 4, No. 2, pp. 105–111, 1993.

Ratnakar B. Mujumdar et al., Cyanine Dye Labeling Reagents Containing Isothiocyanante Groups[1], Cytometry, vol. 10, pp. 11–19, 1989.

Lauren, A. Ernst et al. Cyanine Dye Labeling Reagents for Sulfhydryl Groups[1], Cytometry, vol. 10, pp. 3–10, 1989.

Philip L. Southwick et al. Cyanine Dye Labeling Reagents—Carboxymethylindocyanine Succinimidyl Esters[1], Cytometry, vol. 11, pp. 418–430, 1990.

Alan S. Waggoner et al. A New Fluorescent Antibody Label for Three–Color Flow Cytometry with a Single Laser[a], Reprinted from Clinical Flow Cytometry, vol. 677 of the Annals of the New York Academy of Sciences, pp. 185–193, Mar. 20, 1993.

Jonathan S. Lindsey et al. Visible Light–Harvesting in Covalently–Linked Porphyrin–Cyanine Dyes, Tetrahedron, vol. 45, No. 15, pp. 4845–4866, 1989.

Linda G. Lee, et al., DNA Sequencing with Dye–Labeled Terminators and T7 DNA Polymerase: Effect of Dyes and dNTPs on Incorporation of Dye–Teminators and Probability Analysis of Termination Fragments, Nucleic Acids Research, vol. 20, No. 10, pp. 2471–2483, Apr. 3, 1992.

Amos Carmel, et al., Use of Substrates with Fluorescent Donor and Acceptor Chromophores for the Kinetic Assay of Hydrolases, FEBS Letters, vol. 30, No. 1, Feb. 1973, p. 11.

Robbin DeBiasio, et al., Five–Parameter Fluorescence Imaging: Wound Healing of Living Swiss 3T3 Cells, The Rockefeller University Press, 0021–9525/87/10/1613/10, The Journal of Cell Biology, vol. 105, Oct. 1987, pp. 1613–1622.

Douglas J. Gale, et al., The Amidomethylation and Bromination of Fischer's Base. The Preparation of Some New Polymethine Dyes, Aust. J. Chem., 1977, 30, pp. 689–94.

Frances M. Hamer, The Cyanine Dyes and Related Compounds, 1964.

Vernon T. Oi, Flourescent Phycobiliprotein Conjugates for Analyses of Cells and Molecules, Rapid Communications, The Journal of Cell Biology, vol. 93, Jun. 1982, pp. 981–986.

* cited by examiner

FLUORESCENT LABELING COMPLEXES WITH LARGE STOKES SHIFT FORMED BY COUPLING TOGETHER CYANINE AND OTHER FLUOROCHROMES CAPABLE OF RESONANCE ENERGY TRANSFER

This is a divisional application of application Ser. No. 08/476,880 filed Jun. 7, 1995, now U.S. Pat. No. 6,008,373.

BACKGROUND OF THE INVENTION

1. Field of the Invention

The present invention relates to fluorescent labeling complexes, and more particularly to low molecular weight fluorescent complexes with large Stokes shifts.

2. Description of the Invention Background

Fluorescence labeling is an important technology for detecting biological molecules. For example, antibodies can be labeled with fluorescent dyes. The binding of antibodies to their specific target molecules can then be monitored on the basis of a fluorescence signal, which may be detected with a spectrometer, immunofluorescence instrument, flow cytometer, or fluorescence microscope. In a similar way, DNA sequences can be detected with fluorescence detection instruments after the DNA has been "hybridized" with a complementary DNA sequence that has been labeled with a fluorescent dye.

Very bright and water soluble fluorescent labeling reagents are important for sensitive detection of labeled antibodies, DNA probes, ligands, cytokines, drugs, lipids, metabolites and other molecules and compounds of interest. Multiparameter analysis using fluorescent labels with distinctly different emission wavelengths further increase the importance of this technology by providing a powerful tool for correlating multiple antigenic or genetic parameters in individual cells. In epifluorescence microscopy, a continuous light source with different sets of excitation and emission filters are used to excite and detect each fluorescent species. This approach works especially well if the absorption and emission wavelengths of each of the fluorophores are relatively close together (e.g. Stokes shifts of 15–30 nm). Most of the highly fluorescent, low molecular weight fluorochromes like the cyanines and xanthenes have narrow absorption and emission peaks and small Stokes shifts. Up to 5 separate fluorescent labels have been analyzed on the same specimen by microscopy using epifluorescence filter sets as described in DeBiasio, R., Bright, G. R., Ernst, L. A., Waggoner, A. S., Taylor, D. L. "Five-parameter fluorescence imaging: Wound healing of living Swiss 3T3 cells," Journal of Cell Biology, vol. 105, pp.1613–1622 (1987).

Flow cytometers and confocal microscopes are different from microscopes equipped with separate epifluorescence filter sets, in that they utilize lasers with defined wavelengths for fluorescence excitation. While it is easy to find a single fluorophore that can be efficiently excited at a particular laser wavelength, it is difficult to find additional fluorescent labels with large enough Stokes shifts to provide emission well separated from that of the first fluorophore. The naturally occurring phycobiliproteins are a class of multichromophore fluorescent photosystem proteins that have large wavelength shifts. See, Oi, V. T., Glazer, A. N., Stryer, L. "Fluorescent phycobiliprotein conjugates for analyses of cells and molecules," Journal of Cell Biology, vol.93, pp.981–986 (1982). These can be covalently coupled to antibodies and have become widely used in flow cytometry for 2 color lymphocyte subset analysis. R-phycoerythrin (R-PE), a photosystem protein containing 34 bilin fluorophores which can be excited at 488 nm with the widely available argon ion laser, has been especially useful. It fluoresces maximally at 575 nm. R-PE and fluorescein can both be excited at 488 nm, but R-PE can readily be discriminated with optical band-pass interference filter sets from the fluorescein signal, which appears at 525 nm. Recently, 3-color immunofluorescence by flow cytometry has become possible through the development of tandem conjugate labeling reagents that contain a reactive cyanine fluorescent dye which is excited at 488 nm and fluoresces at 613 nm, and is sold commercially under the name Cychrome. See, U.S. Pat. No. 4,876,190 and Waggoner, A. S., Ernst, L. A., Chen, C. H., Rechtenwald, D. J., "PE-CY 5; A new fluorescent antibody label for 3-color flow cytometry with a single laser," Ann. NY Acad. Sci., vol.677, pp.185–193 (1993). With these tandem fluorophores, energy transfer from excited R-PE to the Texas Red or the reactive pentamethine cyanine known as CY5 leads to fluorescence at 620 nm or 670 nm, respectively.

The phycobiliprotein-based labels are very fluorescent and provide excellent signals in 2 and 3-parameter experiments for detection of cell surface antigens. However, these reagents have not been widely utilized for measurement of cytoplasmic antigens or for detection of chromosomal markers by fluorescence in situ hybridization because their large size (MW=210,000 Daltons) limits penetration into dense cell structures.

There is a need for a new class of low molecular weight fluorescent labels that will provide multicolor fluorescence detection using single wavelength excitation. There is a further need for several such flourescenct labels each of which can be excited optimally at a particular laser wavelength but that fluoresce at significantly different wavelengths.

SUMMARY OF THE INVENTION

The present invention provides a low molecular weight fluorescent labeling complex which includes a first, or donor, fluorochrome having first absorption and emission spectra, and a second, or acceptor, fluorochrome having second absorption and emission spectra. At least one of the first or second fluorochromes is a cyanine dye. The wavelength of the emission maximum of the second fluorochrome is longer than the wavelength of the emission maximum of the first fluorochrome, and a portion of the absorption spectrum of the second fluorochrome overlaps a portion of the emission spectrum of the first fluorochrome for transfer of energy absorbed by the first fluorochrome upon excitation with light to the second fluorochrome.

The complex also includes a linker for covalently attaching the fluorochromes to permit resonance energy transfer between the first and the second fluorochromes. The linker may be flexible and in a preferred embodiment, separates the fluorochromes by a distance that provides efficient energy transfer, preferably better than 75%. The linker may be about 2 to 20 bond lengths. A preferred length for the linker is less than 70 Angstroms (7 nm), and more preferably, less than 20 Angstroms (2 nm). In the case of flexible linkers, particularly when the labeling complexes are in solution, the relative orientations of the first and second fluorochromes changes as the linker flexes.

The first fluorochrome preferably has an extinction coefficient greater than 20,000 Liters/mole cm and preferably greater than 50,000 Liters/mole cm and the second fluorochrome has a fluorescence quantum yield greater than or equal to about 0.05. Quantum yield is generally related to a molecule's rigidity or planarity and indicates the molecules propensity to fluoresce, i.e. to give off energy as light, rather than as heat when energy is provided to the molecule. The combined molecular weight of the fluorochromes and the linker is less than about 20,000; Daltons, and preferably in the range of 500 to 10,000 Daltons.

The complex includes a target bonding group capable of forming a covalent bond with a target compound to enable the complex to label the target, such as a carrier material or a biological compound. The target bonding group may be a reactive group for reacting with a functional group on the target compound or molecule. Alternatively, the complex may contain the functional group and the target may contain the reactive constituent. The reactive group is preferably selected from the group consisting of succinimidyl ester, isothiocyanates, dichlorotriazine, isocyanate, iodoacetamide, maleimide, sulfonyl halide, acid halides, alkylimidoester, arylimidoester, substituted hydrazines, substituted hydroxylamines, carbodiimides, and phosphoramidite. The functional group may be selected from the group consisting of amino, sulfhydryl, carboxyl, hydroxyl and carbonyl. The target may be antibody, antigen, protein, enzyme, nucleotide derivatized to contain one of an amino, hydroxyl, sulfhydryl, carboxyl or carbonyl groups, and oxy or deoxy polynucleic acids derivatized to contain one of an amino, hydroxy, sulfhydryl, carboxyl or carbonyl groups, cells, polymer particles or glass beads. In the alternative embodiment, the target may be derivatized to contain the reactive groups identified above to form covalent bonds with the functional groups on the complex.

The complex preferably also includes water solubilizing constituents attached thereto for conferring a polar characteristic to the complex. They are preferably attached to the aromatic ring of the cyanine fluorochrome. The water solubilizing constituents must be unreactive with the target bonding group of the complex. The solubilizing constituents are preferably selected from the group consisting of amide, sulfonate, sulfate, phosphate, quaternary ammonium, hydroxyl and phosphonate. Water solubility is necessary when labeling protein and oxy or deoxy nucleic acids derivatized with amino groups or sulfhydryl groups in aqueous solutions. A less polar form of the energy transfer compound may bind noncovalently to DNA by intercalation between base pairs or by interaction in the minor groove of DNA. Such compounds would be useful for DNA quantification or localization.

In addition to the embodiment of the invention which includes a single donor and a single acceptor fluorochrome, the fluorescent labeling complex may further include a third fluorochrome having third absorption and emission spectrum and covalently attached to the second fluorochrome. The wavelength of the emission maximum of the third fluorochrome is longer than the wavelength of the emission maximum of the second fluorochrome, and a portion of the emission spectrum of the second fluorochrome overlaps a portion of the absorption spectrum of the third fluorochrome for transferring energy absorbed from the first fluorochrome to the second fluorochrome to the third fluorochrome. Energy transfer procedes consecutively, i.e. in series, from the first to the second to the third fluorochrome.

In an alternative embodiment, the complex may include a plurality of the first fluorochromes each covalently linked to the second fluorochrome and each capable, upon excitation with light, of transferring energy to the second fluorochrome. In another embodiment, the complex may include a plurality of the second fluorochromes each covalently linked to the first fluorochrome and each capable of accepting energy from the first fluorochrome when the first fluorochrome is excited by light. The plurality of first or second fluorochromes may be the same molecule or may be different. For example, there may be several donor fluorochromes which are excitable at different wavelengths to accommodate different excitation light sources. Energy transfer procedes in parallel in these embodiments.

The labeling complexes of the invention are synthesized preferably by covalently linking cyanine fluorochromes to other cyanine fluorochromes to form energy donor-acceptor complexes. Cyanine fluorochromes are particularly useful for preparation of these complexes because of the wide range of spectral properties and structural variations available. See, for example, Mujumdar, R. B., Ernst, L. A., Mujumdar, S. R., Lewis, C., Waggoner, A. S. "Cyanine dye labeling reagents. Sulfoindocyanine succininmidyl ester," Bioconjugate Chemistry, vol.4, pp.105–111 (1993) and U.S. Pat. No. 5,268,486 to Waggoner et al., the disclosure of which is incorporated herein by reference.

The invention also includes a reagent and a method for making the reagent including incubating the fluorescent water soluble labeling complex described above with a carrier material One of the complex or the carrier material has a functional group that will react with a reactive group of the other of the complex or the carrier material to form a covalent bond there between. The carrier material can be selected from the group consisting of polymer particles, glass beads, cells, antibodies, antigens, protein, enzymes, nucleotide derivatized to contain one of an amino, sulfhydryl, carbonyl, carboxyl or hydroxyl groups, and oxy or deoxy polynucleic acids derivatized to contain one of an amino, sulfhydryl, carboxyl, carbonyl or hydroxyl groups. Alternatively, the carrier material may contain the reactive groups and the fluorescent labeling complex of the invention may contain any of the aforementioned functional groups that will react with the reactive groups to form covalent bonds.

In an alternative embodiment, the fluorescent complexes of the invention need not have a reactive group when used to noncovalently bind to another compound. For example, the complex may be dissolved, then mixed in an organic solvent with a polymer particle, such as polystyrene, then stirred by emulsion polymerization. The solvent is evaporated and the fluorescent dye complex is absorbed into the polystyrene particles.

BRIEF DESCRIPTION OF THE DRAWINGS

The present invention will be better understood by reference to the drawings in which.

DETAILED DESCRIPTION OF THE PREFERRED EMBODIMENTS

Figure 1:
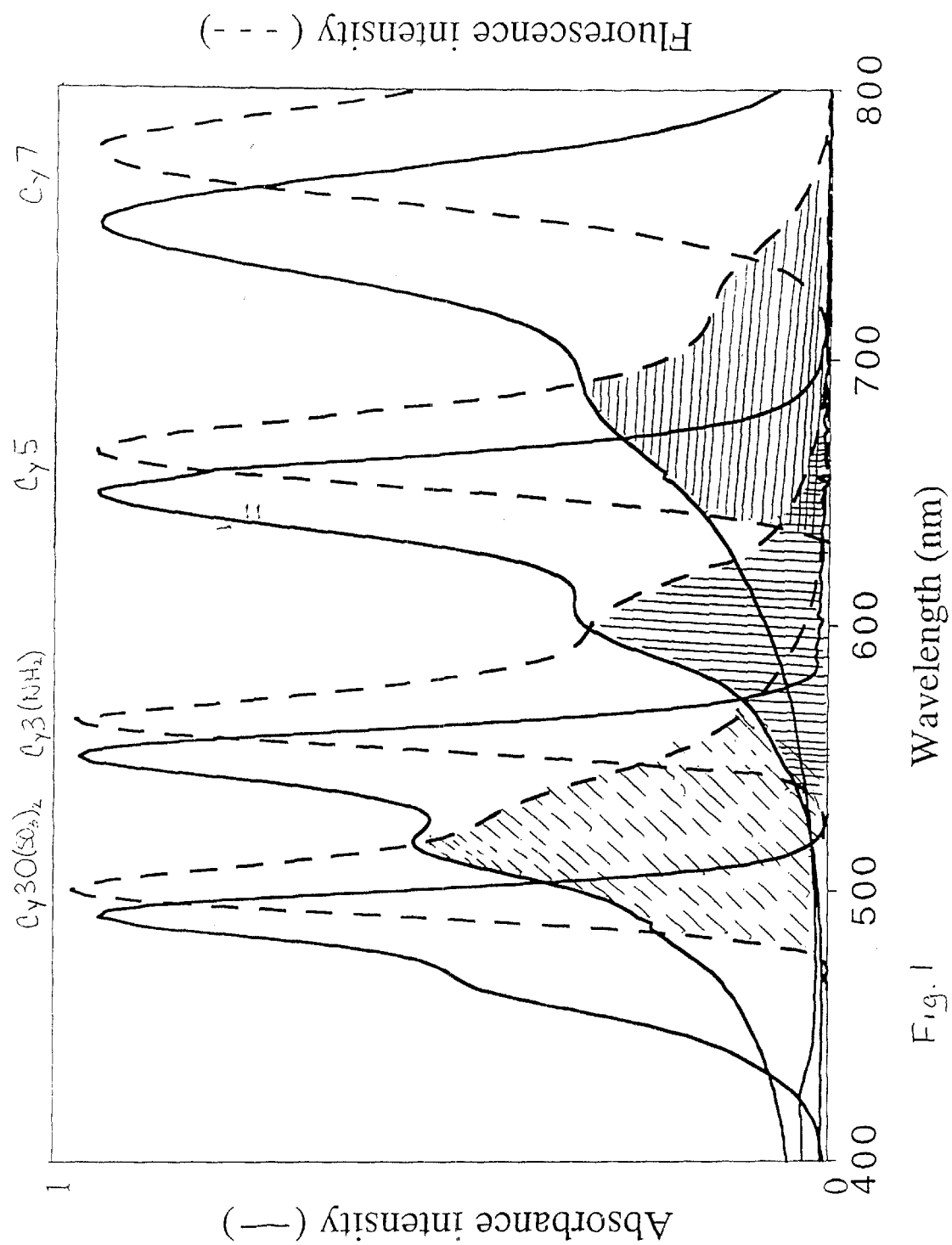
FIG. 1 is a schematic illustration of the overlapping absorption and emission spectra of four cyanine fluorochromes that can be used in the energy transfer labeling complex of the present invention.

The present invention provides low molecular weight, preferably water soluble, fluorescent labeling complexes with large excitation-emission wavelength shifts or Stokes shifts. For purposes of the present specification, the Stokes shift of the fluorescent complex is the absolute difference in nanometers between the absorbance maximum of the lowest light absorber of the complex and the fluoresence of the longest wavelength emitter of the complex. The complexes, as briefly explained above, contain two or more fluorochromes linked together for transfer of energy from a shorter wavelength to a longer wavelength. As shown schematically in FIG. 1, the first, donor fluorochrome absorbs energy upon excitation at an excitation wavelength (solid line) within its absorbance spectrum and emits energy at a wavelength within its emission spectrum (broken line). When linked at an appropriate orientation to a second, acceptor fluorochrome, the donor fluorochrome transfers, or donates, the energy of its excited state to the acceptor fluorochrome at a wavelength within the absorbance spectrum (solid line) of the acceptor fluorochrome. The acceptor fluorochrome absorbs the donated energy and emits it at a wavelength within its emission spectrum (broken line), which as shown, is longer than the longest wavelength of the emission spectra of the donor fluorochrome. It is important, therefore, that the emission spectrum of the donor fluorochrome overlap with the absorption spectrum of the acceptor fluorochrome. The overlapping areas are shown by hatched lines. The greater the overlap, the more efficient the energy transfer.

The complexes include at least one cyanine fluorochrome, and preferably at least one polymethine cyanine dye. The cyanines are particularly useful due to the wide range of spectral properties and structural variations available. Several such complexes will be described for purposes of this detailed description. Other low molecular weight fluorochromes in addition to the cyanine fluorochromes, such as the fluoresceins, pyrene trisulfonates, which are sold under the trade mark cascade blue, rhodamines and derivatives of the bispyrromethene boron-difluoride dyes, such as 3,3', 5,5'-tetramethyl 2,2'-pyromethene-1,1'-boron-difluoride, sold under the trademark BODIPY by Molecular Probes, Inc., can be used to form the fluorescent labeling complexes of the invention. BODIPY analogs are disclosed in U.S. Pat. Nos. 4,774,339, 5,187,223, 5,248,782 and 5,274,113, all to Haugland and Kang, as well as in "Handbook of Fluorescent Probes and Research Chemicals" compiled by Haugland and published by Molecular Probes, Inc.

The fluorescent labeling complexes of the invention have low molecular weights and can be readily conjugated to antibodies, other proteins, and DNA probes. Low molecular weight as used herein shall mean that the combined molecular weight of the fluorochomes and linker of the complex is less than about 20,000 Daltons, and preferably between about 500 and 10,000 Daltons, and for a two fluorochrome complex, preferably in the range of 1000 to 2500 Daltons. Therefore, these labeled species will have much greater penetration into intracellular environments than is possible with the large phycobiliprotein labels currently in use. The low molecular weight fluorescent labeling complexes of the invention should be valuable not only for flow cytometry, but also for laser confocal microscopy and for other detection systems requiring multicolor detection with single wavelength excitation.

Many structural varieties and modifications of cyanines are possible. By varying the number of carbons in the methine bridge of the cyanine dyes and the heteroatoms or other constituents on the cyanine dyes, a variety of different spectral qualities can be achieved. The cyanine dyes are especially well adapted for the analysis of a mixture of components wherein dyes of a variety of emission wavelengths are required because specific cyanine and related dyes can be synthesized having a wide range of excitation and emission wavelengths. Specific cyanine and related dyes have specific excitation and emission wavelengths can be synthesized by varying the number of methine groups or by modifying the cyanine ring structures. In this manner, it is possible to synthesize dyes having particular excitation wavelengths to correspond to a particular excitation light source, such as a laser, e.g., a HeNe laser or a diode laser. Therefore, energy transfer labels can be made that absorb and emit efficiently at most wavelengths in the visible region of the spectrum. Commonly used sources of excitation excite at laser line 488 nm. Therefore, that exemplary excitation wavelength will be used for purposes of the description of the invention. Those in the art will recognize that other energy transfer labels can be made for specific excitation sources without departing from the scope of this invention.

The energy transfer between donor and acceptor fluorochromesl that are appropriately selected and linked can be very efficient The complexes prepared and described herein show energy transfer ranging from 50 to 99% efficiency. Energy transfer efficiency depends on several factors such as spectral overlap, spatial separation between donor and acceptor, relative orientation of donor and acceptor molecules, quantum yield of the donor and excited state lifetime of the donor.

Complexes may be constructed using rigid linkers that optimally orient the transition moments of the donor and acceptor chromophores. Alternatively, the linker may be flexible. For optimal energy transfer to occur, the transition moments of the first and second fluorochromes are oriented relative to each other in a nonperpendicular direction. Transition moments positioned generally parallel or in tandem relative to each other provide efficient transfer. In practice, the fluorochromes are not in a static position. The nonrigid linker covalently binding the fluorochromes flexes, particularly when the complexes are in solution. The transition moments of the fluorochromes will change as the linker flexes, but, provided the donor and acceptor transition moments are nonperpendicular during the excited state lifetime of the donor, energy transfer will occur.

Shorter linkers would enhance transfer, since efficiency varies as the inverse 6th power of separation of the centers of the chromophores according to Forster's Equation:

$$ET \alpha K^2 \Phi_D J / R^6 \pi_D$$

where ET is energy transfer; $K^2$ is the relative orientation of donor and acceptor transition moments; $\Phi_D$ is the quantum yield of the donor molecule; R is the distance between the centers of the donor and acceptor fluorochromes; J is the overlap between the emission spectrum of the donor and the absorption spectrum of the acceptor fluorochromes; and $\pi_D$ is the excited state life time of the donor molecule. See, Forster, T., "Intermolecular Energy Transfer and Fluorescence," Ann. Physik., vol.2, p.55 (1948). The distance R between the centers of the two fluorochromes, e.g., in a complex having two cyanine dyes, the middle of the methine bridge of one cyanine to the middle of the methine bridge of the second cyanine, along the length of the compounds may be from 10 to about 80 Angstroms. The length of the linker connecting the fluorochromes, as used herein, is different from the distance R. The linker should permit resonance energy transfer between the fluorochromes. The fluorochromes should not interact chemically or form secondary bonds with each other. A preferred length for the linker is less than 70 Angstroms (7 nm), and more preferably, less than 20 Angstroms (2 nm). In terms of bond length, the linker may be from 2 to 20 bond lengths. For example, if the linker includes an alkyl chain, —$(CH_2)_n$—, the carbon number n may be from 1 to about 15. As n exceeds 15, the efficiency of the energy transfer decreases. The linker may include part of the constituents extending from the cyanine dye. In other words, the linker is attached to the dye chromophore, but is not a part of it. For example, referring to the linker shown in Table 1, some extend from the ring N in one cyanine to a functional group on the benzene ring of the other cyanine. Some extend between functional groups on the benzene rings of linked dyes. The linker is placed on one cyanine dye before the dye linker combination is attached to the second dye. With a relatively short linker and optimal orientation, there may be efficient resonance energy transfer even when the spectral overlap becomes small. Therefore, it is possible to obtain larger wavelength shifts even when only two chromophores are used in the complex.

The fluorescent labeling complexes include groups capable of forming covalent bonds with corresponding groups on target compounds. Preferably, reactive groups are on the complex and functional groups are on the target compound or molecule. However, those skilled in the art will recognize that the functional groups may be placed on the complex and the reactive groups may be on the target.

The reactive groups of the complexes of the invention include succinimidyl esters, isothiocyanates, dichlorotriazine, isocyanate, iodoacetamide, maleimide, sulfonyl halide, alkylimidoester, arylimidoester, carbodiimide, substituted hydrazines, hydroxylamines, acid halides and phosphoramidite. The reactive groups will form covalent bonds with one or more of the following functional groups: amine, hydroxyl, sulfhydryl, carboxyl and carbonyl.

To promote water solubility, water solubilizing constituents may be attached to the complex or to the linker. They include amide, sulfonate, sulfate, phosphate, quaternary ammonium, hydroxyl and phosphonate groups. Sulfonate or sulfonic acid groups attached directly to the aromatic ring of the cyanine fluorochrome are preferred.

Examples of some of the dyes that can be used as donor and acceptor fluorochromes in the fluorescent labeling complexes of the invention are shown in Table 1 below:

TABLE 1

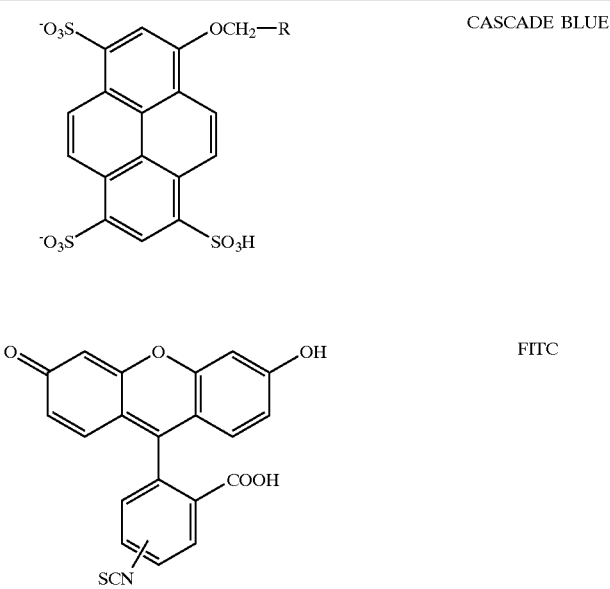

TABLE 1-continued
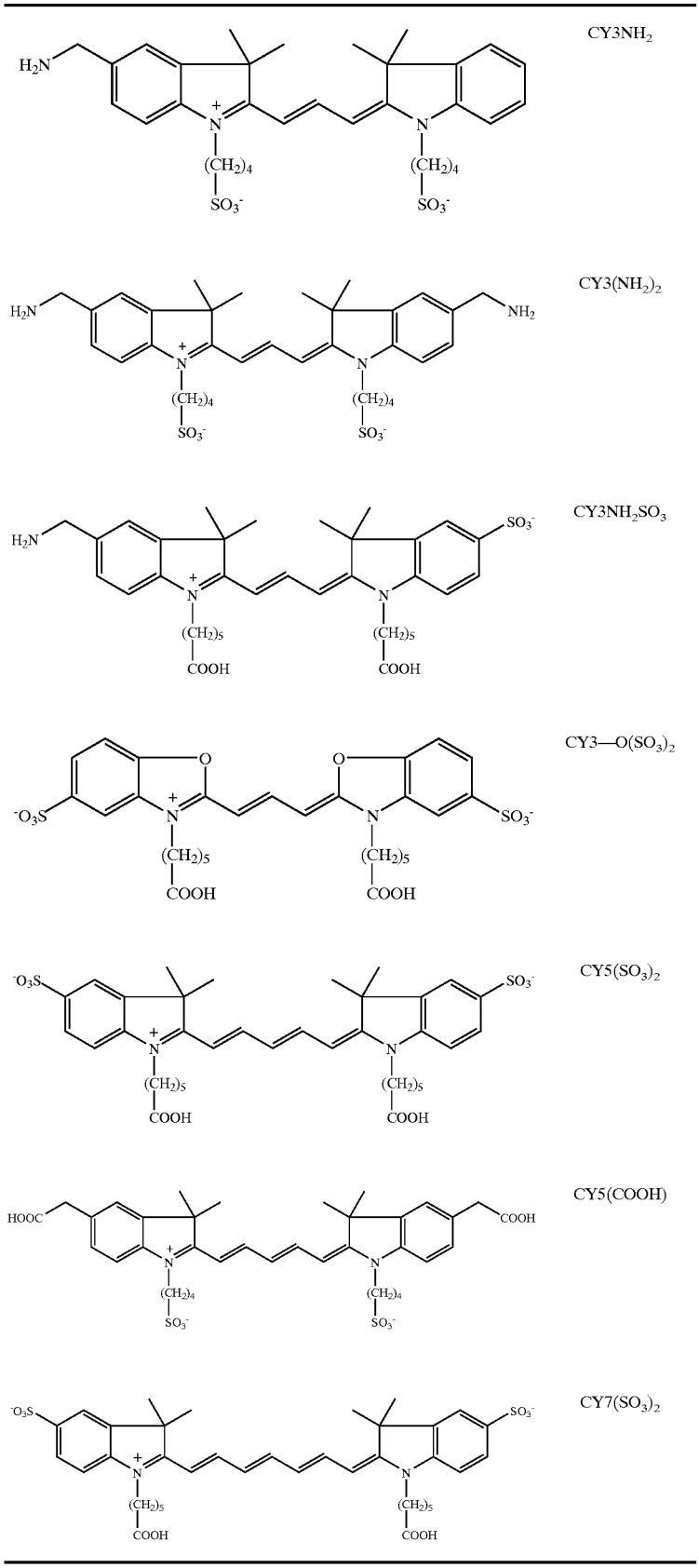

Additional cyanines for use in the complexes of the invention are the rigidized monomethine cyanines disclosed in the copending applications of the Ratnakar Majumdar, Bhalchandra Karandikar and Alan S. Waggoner entitled "Rigidized Monomethine Cyanines" Ser. No. 08/474,056 filed Jun. 7, 1995, and "Monomethine Cyanine Rigidized by a Two-Carbon Chain", filed on even date herewith Ser. No. 08/474,057 filed Jun. 7, 1995, the disclosures of which are incorporated herein by reference. The monomethine rigidized dyes have the general structures

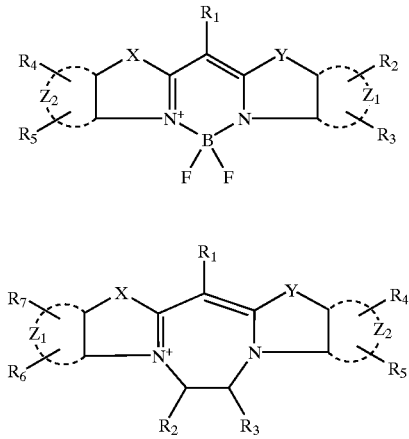

The boron rigidized monomethine cyanine dyes have sharp distinct absorptive and emissive signals, and are photostable. Certain of the boron-rigidized monomethine cyanines maximally absorb and emit light at wavelengths between 400–500 nm or less and fluoresce in the blue region of the visible spectrum.

Experiments have demonstrated that for obtaining exceptionally large excitation-emission wavelength shifts, it is possible to use sequential energy transfer steps in the complex. For example, three chromophores have been linked to provide maximal emission at the wavelength of a cyanine dye, the heptamethine cyanine designated CY7 in Table 1 above (780 nm) with excitation at 488 nm. The initial donor was fluorescein and the intermediate fluorophore in this complex was a trimethine cyanine dye designated generally as CY3. The fluorescein was excited at 488 nm and transferred nearly 100% of its excited state energy to the trimethine cyanine, which in turn transferred about 90% of its excited state energy to the CY7, fluorescing at 782 nm. The same efficiency was observed when a penthamethine cyanine, CY5 was used in place of CY7, with fluorescence at 667 nm. The development of such multichromophore complexes is particularly useful for multicolor detection systems.

Although several of the complexes show efficient energy transfer, the overall quantum yield of these labeling complexes can be further improved. For example, the use of acceptor dyes with quantum yields higher than that of CY5 (see Table 1) would improve the overall "brightness" of the complex.

An experiment was done to determine if two cyanine fluorochromes could be covalently linked for energy transfer. The cyanines used were CY5 and CY7 without reactive groups. The results demonstrated that the cyanines could be covalently linked. The procedure is presented schematically below. The dyes are represented by boxes.

EXAMPLE 1

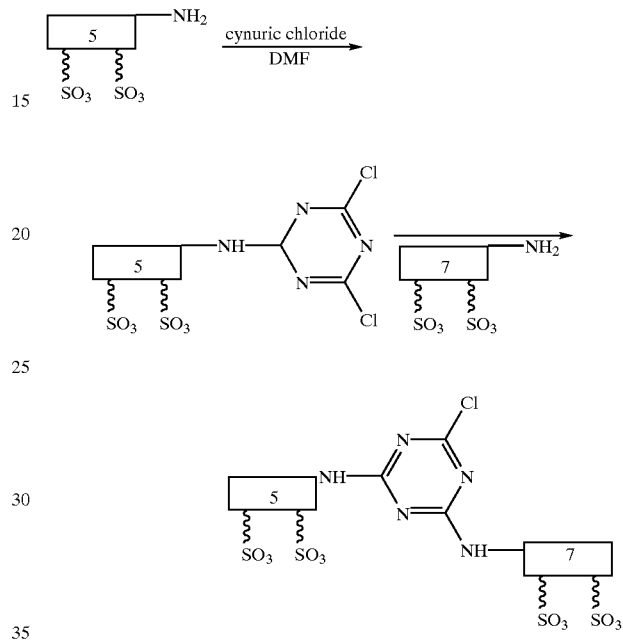

1. 5 mg cyanuric chloride (trichlorotriazine), 2 mg NaHCO$_3$, and 0.25 mL purified dimethyl formamide (DMF) as solvent were mixed at 0° C. To this solution was added 5 mg of amino-cyanine-5 dye represented above by the box containing number 5, and the mixture was stirred at 0° C. for 10 min. Stirring was continued overnight at room temperature. Thin layer chromatography (TLC) revealed one major spot and two minor spots; the latter spots were determined to be impurities. UV-visible absorption showed a peak at 664 nm with a shoulder at 605 nm.

2. The reaction mixture was worked up by precipitation with ether. A dark blue powder was obtained. 0.3 mL DMF was added to dissolve the powder. Then 2 mg of sodium bicarbonate and 4.7 mg of amino-CY7 dye, represented above by the box containing number 7, were added. The mixture was stirred at room temperature for 24 hrs. Absorption peaks showed at 650 nm (with a shoulder at G607 nm) and 761 nm. The reaction was precipitated by several washes with ether, providing a dark powder.

Following the initial success of the above experiments, six energy donor-acceptor complexes were prepared from cyanine fluorochromes in order to investigate the energy transfer efficiency of such compounds. The structures of these complexes are shown in Table 2 and their spectral properties are described in Table 3.

TABLE 2
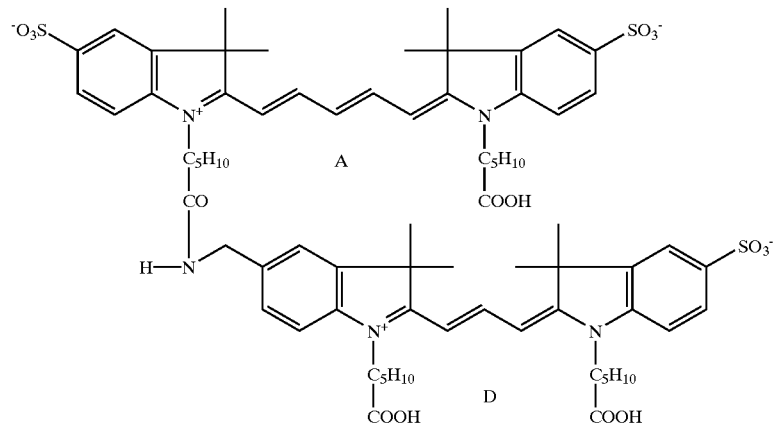
1
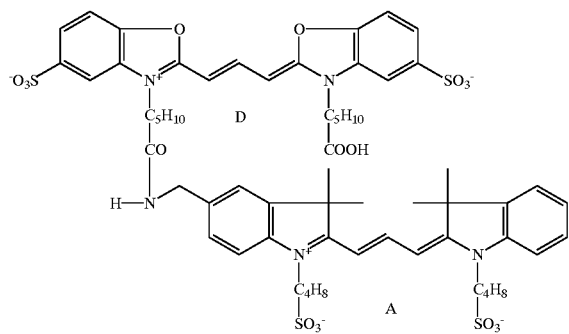
2
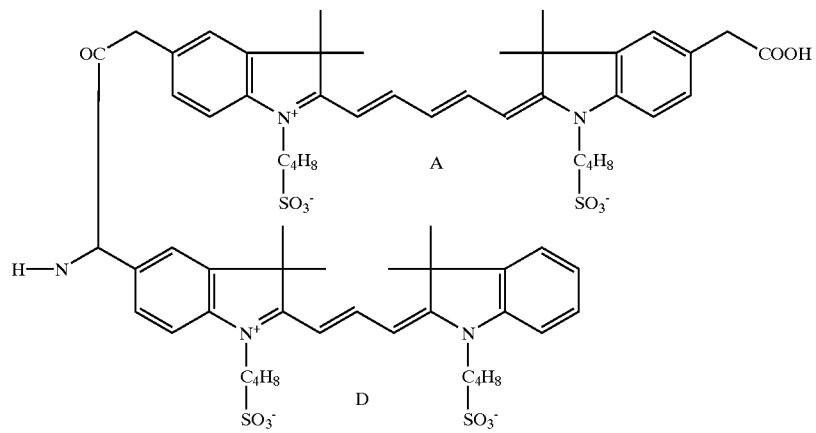
3

TABLE 2-continued

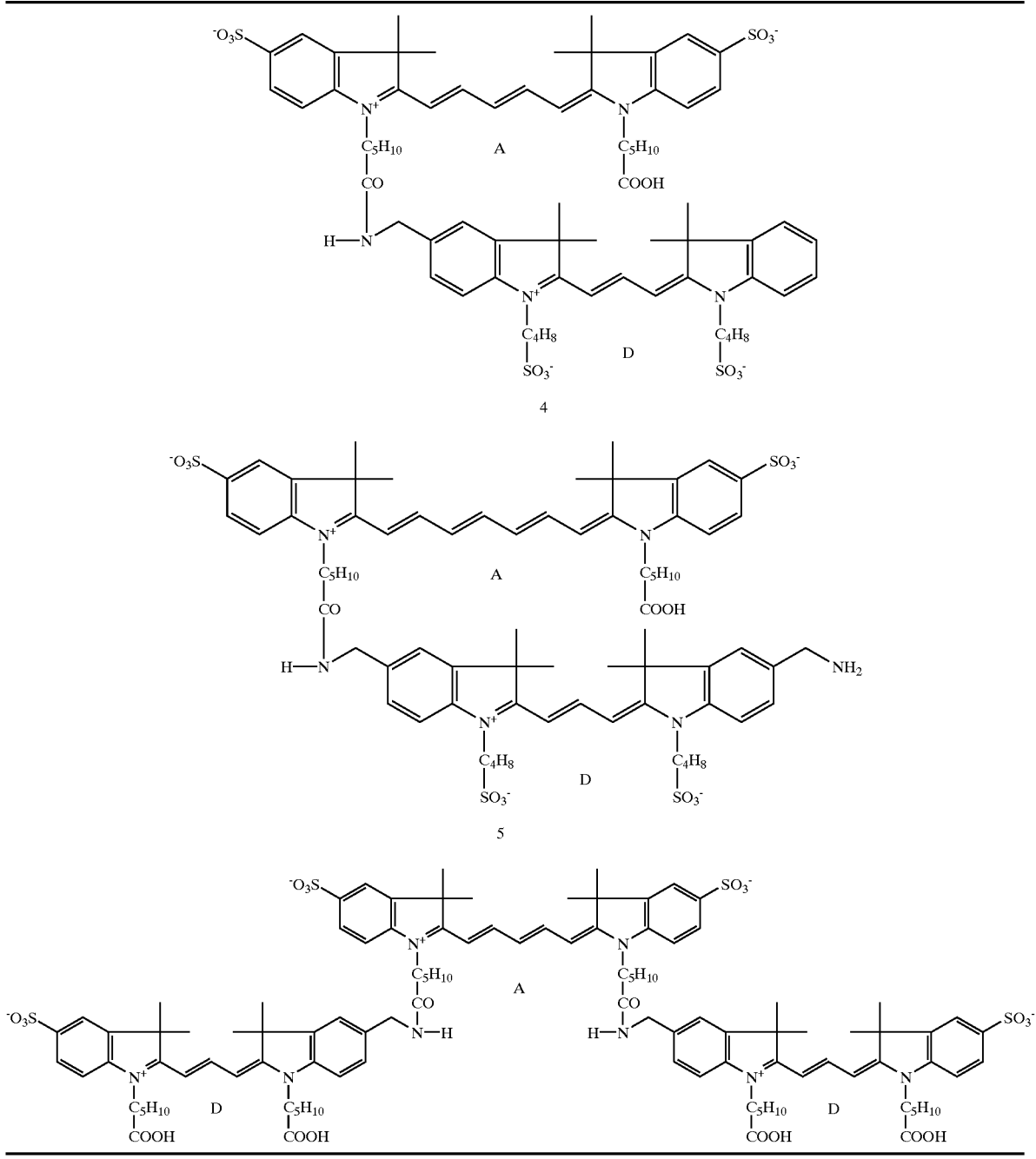

"A" designates the fluorochrome that acts as the energy acceptor and "D" designates the fluorochrome that acts as the energy donor.

The energy transfer complexes shown in Table 2 are as follows: Complex 1, $CY3NH_2SO_3$ (Donor)+CY5 $(SO_3)_2$ (Acceptor); Complex 2, CY3 —O$(SO_3)_2$ (Donor)+CY3NH$_2$ (Acceptor); Complex 3, CY3NH$_2$ (Donor)+CY5COOH (Acceptor); Complex 4, CY3NH$_2$ (Donor)+CY5 $(SO_3)_2$ (Acceptor); Complex 5, CY3 $(NH_2)_2$ (Donor)+CY7 $(SO_3)_2$ (Acceptor); Complex 6, 2 CY3NH$_2$SO$_3$ (Donor)+CY5 $(SO_3)_2$ (Acceptor).

TABLE 3

Spectral Properties Of Cyanine Dyes Used AS Precursors For The Fluorescent Energy Transfer Labeling Complexes Of The Invention.

| Dye | Solvent | Absorption maximum (nm) | Emission maximum (nm) | Quantum yield (φ) |
|---|---|---|---|---|
| Amine containing Cyanine Dyes | | | | |
| CY3NH$_2$ | Methanol | 552 | 569 | 0.05 |
| | PBS | 548 | 563 | 0.05 |

TABLE 3-continued

Spectral Properties Of Cyanine Dyes Used AS Precursors For The Fluorescent Energy Transfer Labeling Complexes Of The Invention.

| Dye | Solvent | Absorption maximum (nm) | Emission maximum (nm) | Quantum yield ($\phi$) |
|---|---|---|---|---|
| $CY3(NH_2)_2$ | Methanol | 552 | 569 | 0.05 |
| | PBS | 548 | 563 | 0.05 |
| $CY3NH_2SO_3$ | Methanol | 556 | 573 | 0.08 |
| | PBS | 548 | 653 | 0.09 |
| Carboxyalkyl containing Cyanine Dyes | | | | |
| CY5COOH | Methanol | 658 | 685 | 0.22 |
| | PBS | 648 | 667 | 0.13 |
| $CY5(SO_3)_2$ | Methanol | 658 | 677 | 0.4 |
| | PBS | 650 | 667 | 0.27 |
| $CY3O(SO_3)_2$ | Methanol | 492 | 506 | 0.20 |
| | PBS | 486 | 500 | 0.09 |
| $CY7(SO_3)_2$ | Methanol | 758 | 789 | ND[a] |
| | PBS | 750 | 777 | ND[a] |

[a]ND means not determined. PBS means phosphate-buffered saline.

The efficiency of energy transfer was estimated by calculating the amount of quenching of donor fluorescence that occurs (DQE) when the acceptor is attached. It is possible that some quenching could occur by pathways other than resonance energy transfer when the acceptor is bound. However, the cyanine; donor preferred for the fluorescent labeling complexes of the present invention are relatively insensitive to their molecular environment. Furthermore, addition of large substituents to trimethine cyanines usually increase, rather than decreases, their fluorescence. Therefore, DQE may be equal to the efficiency of energy transfer. The estimated energy transfer efficiencies based on DQE measurements ranged from 50% to 99% and the wavelength shifts between the donor absorption maxima and the terminal acceptor emission maxima (DI) varied between 83 nm and 294 nm.

Figure 2A:
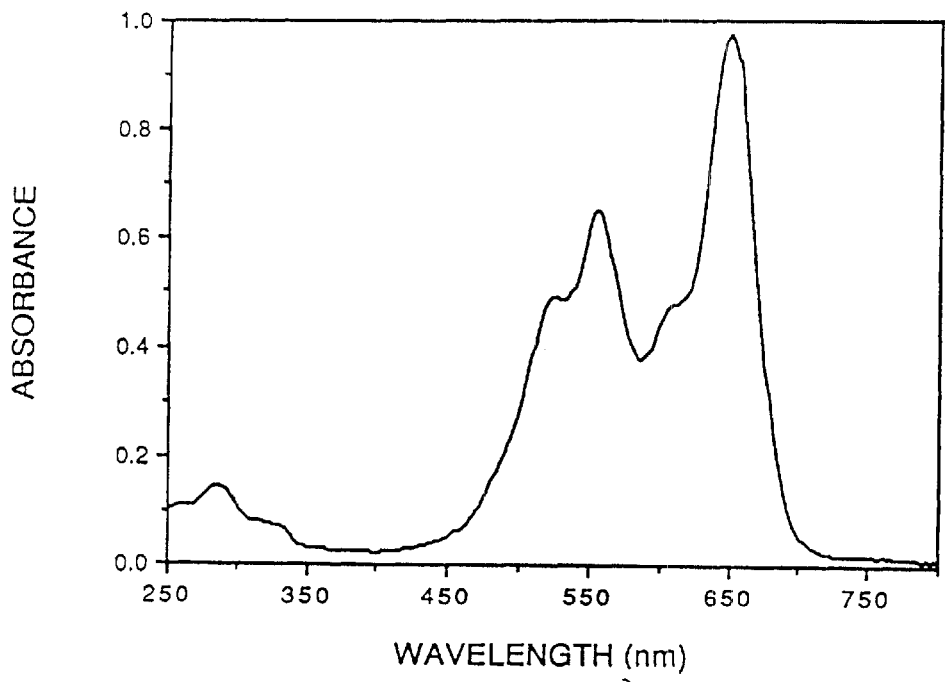
FIG. 2(a) is the absorbance spectrum for the complex consisting of a trimethine and a pentamethine cyanine in a 1:1 ratio in methanol
Figure 2B:
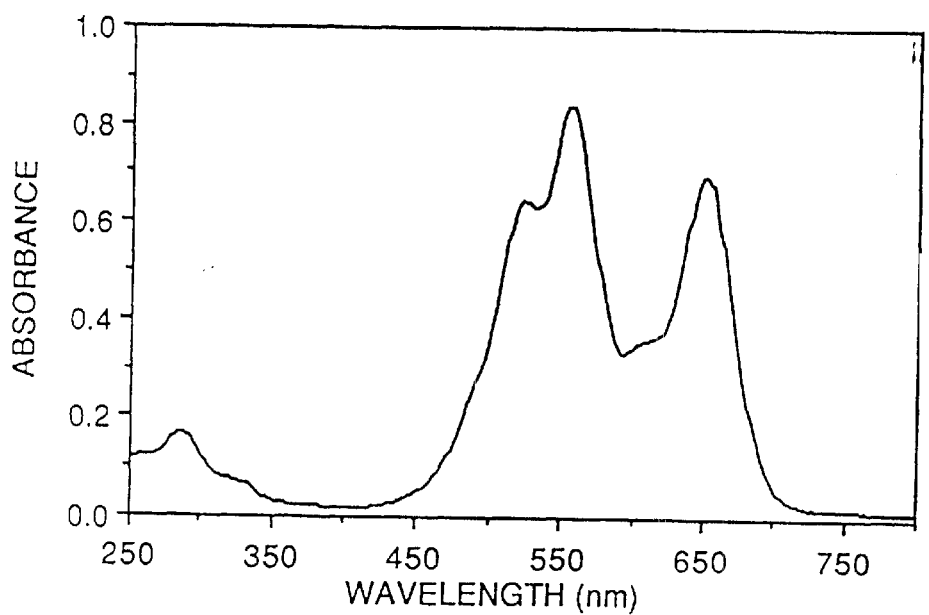
FIG. 2(b) is the absorbance spectrum for the complex consisting of a trimethine and a pentamethine cyanine in a 2:1 ratio in methanol.
Figure 3:
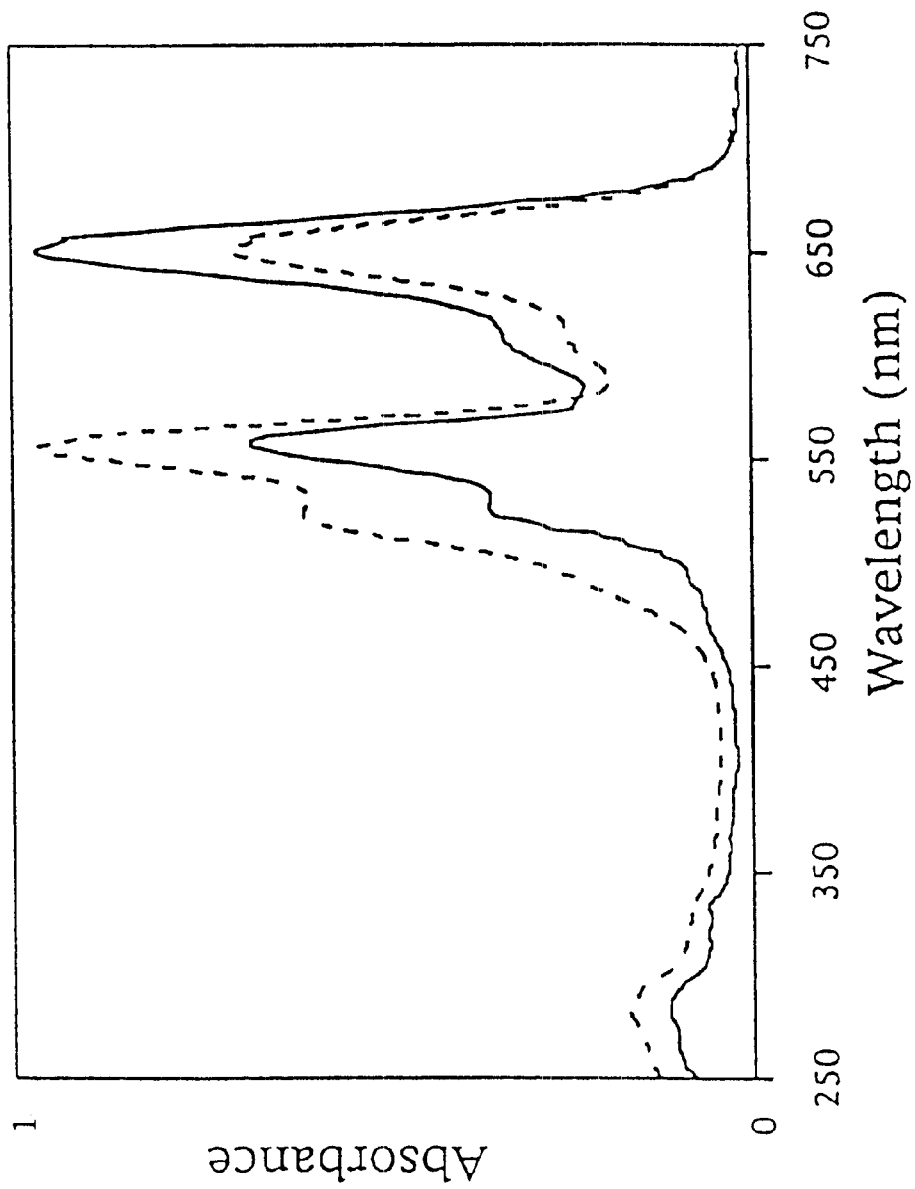
FIG. 3 illustrates the absorption spectra of two fluorescent labeling complexes, complex 1 (solid) in methanol, comprised of one cyanine donor and one cyanine acceptor, and complex 6 (dotted) in methanol, comprised of two cyanine donors and one cyanine acceptor.

Two of the complexes, 1 and 6, are capable of absorbing light at the argon laser wavelength, 488 nm. Complex 1 contains a single donor and single acceptor, and complex 6 contains 2 donors per acceptor. Complex 1 has 3 carboxyl groups and complex 6 has 4 carboxyl groups. These are converted to succinimidyl active esters upon activation. FIG. 3 shows the absorption spectra of complex 1 and complex 6 in methanol. The spectra of the complexes are almost superimposable on absorption spectra obtaining by mixing 1:1 and 2:1 parts of the individual fluorochromes, CY3 and CY5, respectively, as shown in FIGS. 2(a) and 2(b).

Figure 4:
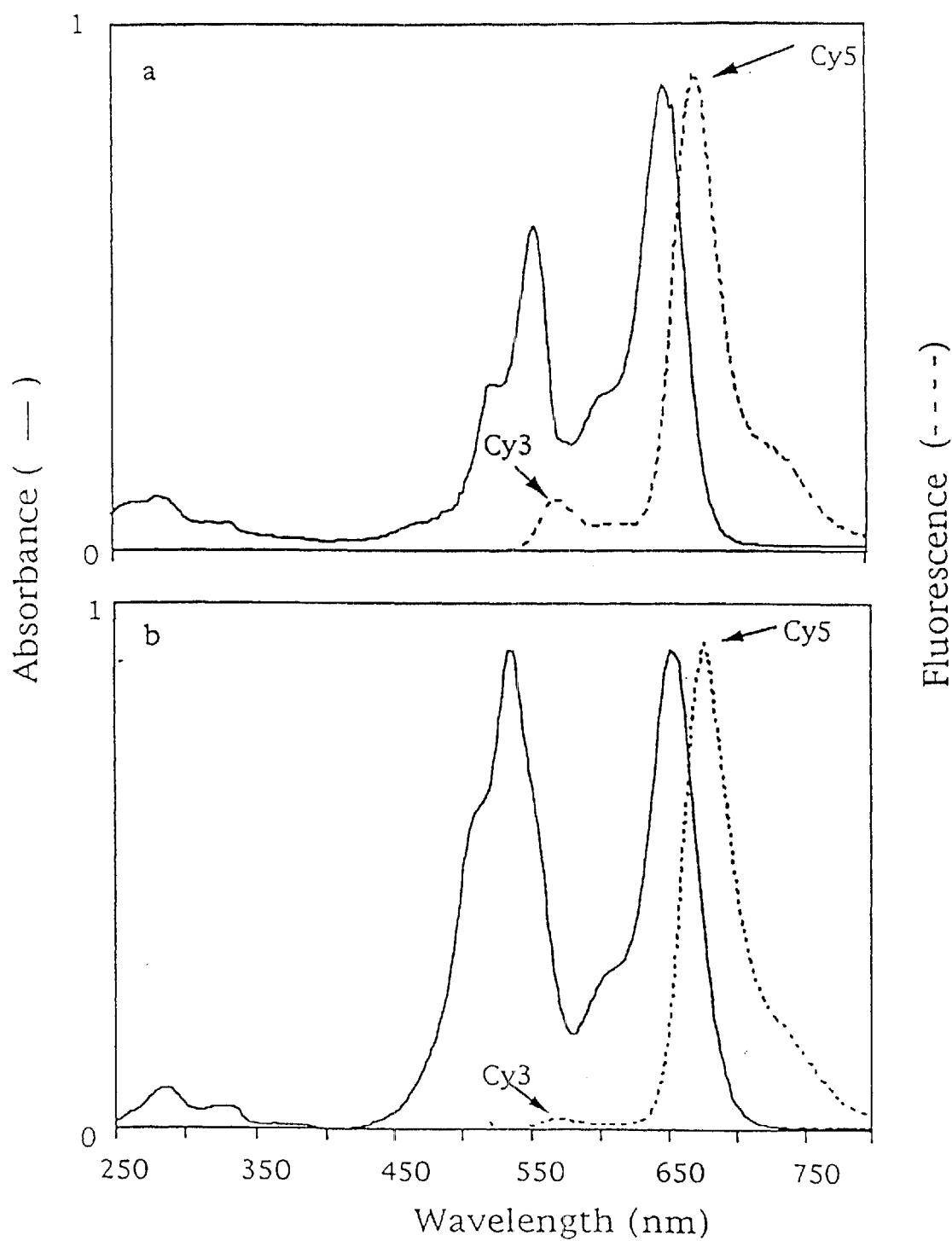
FIGS. 4(a) and (b) illustrate the absorbance (solid) and fluorescence (dotted) spectra of complex 1 of the invention made of trimethine and pentamethine cyanine dyes in (a) methanol and (b) PBS.

Complex 1 was selected for further studies. As shown in FIGS. 4 a and b, the absorbance (solid line) of complex 1 varies slightly in phosphate buffer saline (FIG. 4b) and methanol (FIG. 4a) but fluorescence remains unchanged. The emission of the donor component at 572 nm is very weak compared with the emission of the acceptor at 675 nm, as would be expected when energy transfer is efficient.

Figure 6:
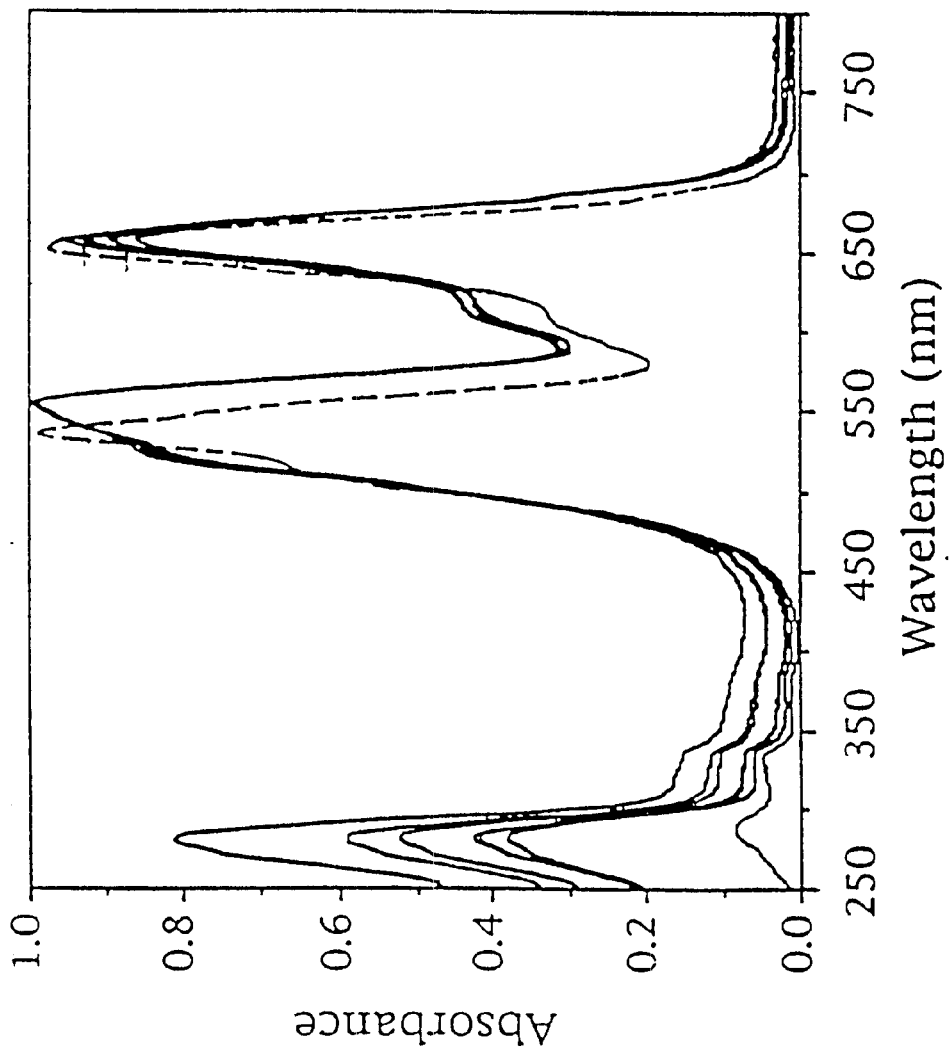
FIG. 6 illustrates the absorbance spectra in PBS of Sheep IgG-complex 1 conjugates at various dye:protein ratios demonstrating that no dimer formation involving either donor or acceptor is evident with increasing dye:protein ratios; and, FIG. 7 illustrates the two color flow cytometry analysis of human lymphocytes labeled with anti-CD4-PE and anti-CD3-streptavidin- complex 1 to mark the helper cell subset of T-cells and total T-cell subset, respectively, showing a subset of complex 1 labeled cells without the PE signal and a second subset of complex 1 labeled cells that is PE stained.

FIG. 6 demonstrates that sheep antibodies can be readily labeled with the activated complex 1. Conjugates made of complex 1 conjugated to sheep IgG at various dye:protein ratios were tested. The lowest dye:protein ratio is represented by the line having its first peak (at about 270 nm) at 0.8 and the highest dye:protein ratio is represented by the line having its first peak (at about 270 nm) at a little less than 0.4. No dimer formation involving either the donor or the acceptor fluorochromes was observed with increasing dye:protein ratios. Each complex 1 contains up to 3 reactive groups. More reactive groups may be used provided no cross-liking occurs. It is important to use labeling conditions that avoid protein cross-linking which quench the fluorescence. Cross-linking by doubly activated cyanines has been observed previously by Southwick, P. L. et al., "Cyanine Dye Labeling Reagents: Carboxymethylindocyanine succinimidyl esters, " Cytometry, vol.11, pp.418–430 (1990) and can be minimized by limiting the concentration of protein to be labeled to approximately 1 mg/mL.

Upon binding to antibodies, the quantum yield of the complex was enhanced three fold as shown in Table 4.

TABLE 4

Spectral Properties Of Energy Transfer Complexes.

| Dye | Absmax nm (ex 10[4]) | Excitation Wavelength (nm) | Emmax (nm) | Quantum Yield ($\phi$) | Energy transferred (%) | Wavelength Shift (nm) |
|---|---|---|---|---|---|---|
| Complex 1[a] | 556 (9.5), 652 (14.3) | 488 | 675 | 0.32 | 91 | 119 |
| | | 514 | 676 | 0.37 | 92 | 120 |
| | | 600 | 673 | 0.49 | — | — |
| Complex 1[b] | 536 (16), 658 (16) | 488 | 675 | 0.03 | 89 | 139 |
| | | 514 | 673 | 0.04 | 89 | 137 |
| | | 600 | 668 | 0.21 | — | — |
| Complex 1PBS[c] | 558, 658 | 488 | 674 | 0.11 | 95 | 116 |
| | | 514 | 673 | 0.13 | 95 | 116 |
| | | 600 | 676 | 0.14 | — | — |
| Complex 1[d] | 562, 658– | 488 | 674 | 0.19 | | |
| | | 514 | 674 | 0.32 | | |
| | | 600 | 674 | 0.39 | | |
| Complex 2[a] | 490 (13), 554 (9.5) | 466 | 571 | 0.15 | 89 | 81 |
| Complex 3[a] | 545 (9.5), 658 (14.3) | 514 | 679 | 0.08 | 83 | 133 |
| Complex 4[a] | 550 (9.4), 656 (14.2) | 514 | 674 | 0.2 | 96 | 124 |
| Complex 5[a] | 445 (9.5), 754 (14.4) | 520 | 782 | N.D. | 99 | 226 |
| Complex 6[a] | 556 (9.5), 652 (14.4) | 488 | 674 | 0.23 | 49 | 118 |
| | | 514 | 674 | 0.24 | 50 | 118 |
| | | 600 | 674 | 0.34 | — | — |

TABLE 4-continued

Spectral Properties Of Energy Transfer Complexes.

| Dye | Absmax nm (ex 10⁴) | Excitation Wavelength (nm) | Emmax (nm) | Quantum Yield (φ) | Energy transferred (%) | Wavelength Shift (nm) |
| --- | --- | --- | --- | --- | --- | --- |
| Complex 6[b] | 548 (20.0), 652 (15.0) | 488 | 566 | 0.05 | 43 | 118 |
|  |  | 514 | 564 | 0.05 | 38 | 116 |
|  |  | 600 | 668 | 0.23 | — | — |

[a]In methanol,
[b]In PBS
[c]Complex 1 on streptavidin, d/p = 4
[d]In glycerine
N.D. means not determined It is believed that this occurs because the radiationless deactivation pathway of both the CY3 and CY5 components of complex 1 are reduced because of their restricted mobility when bound to the surface of the protein. Other means of restricting conformational mobility are known to increase the fluorescence efficiency of cyanine fluorochromes, as described in Mujumdar, R. B. et al. "Cyanine dye labeling reagents. Sulfoindocyanine succininmidyl ester," Bioconjugate Chemistry, vol.4, pp.105–111 (1993). In fact, when complex 1 was dissolved in glycerine, the quantum yield increased by several fold as shown in Table 3.

Figure 7:
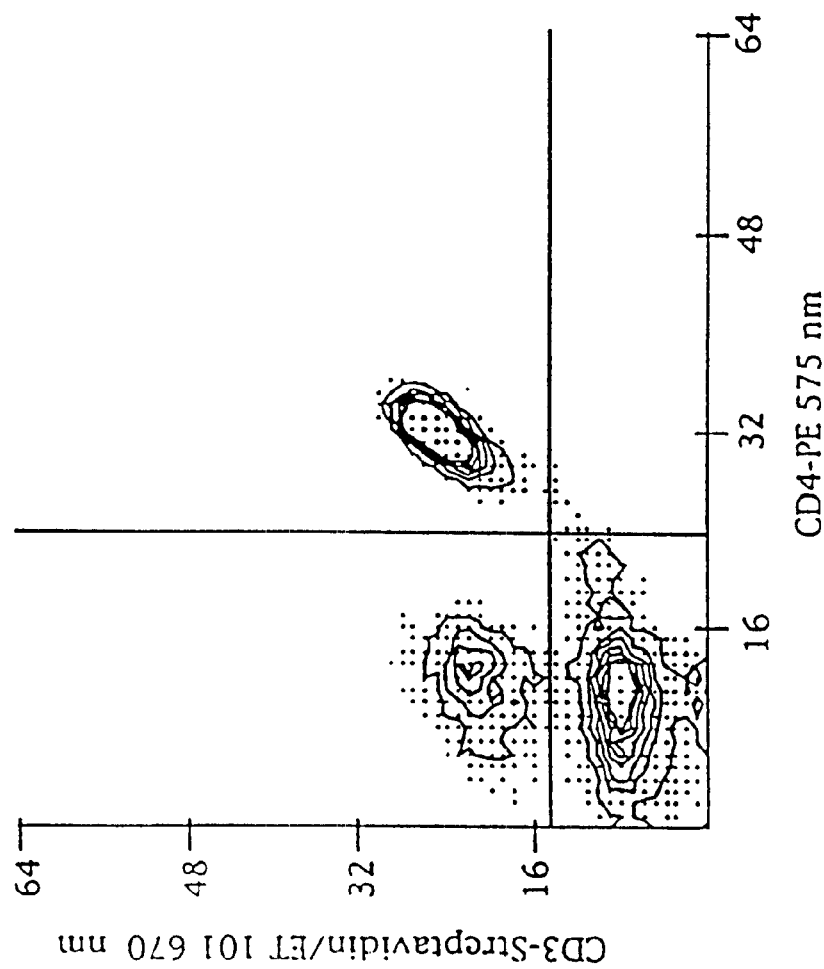

Activated complex 1 can be used as a fluorescence label for 2 color flow cytometry experiments with 488 nm excitation. The scatter plot is shown in FIG. 7. Human T-lymphocytes were used to compare the complex 1 label with another 2-color reagent, R-Phycoerythrin, which also excites at 488 nm and emits at 575 nm. Complex 1 labeled streptavidin (fluorochrome/protein~4) was used to detect biotinylated CD3 antibody, which marks all T-cells. In the same lymphocyte sample, Phycoerythrin(PE)-labeled anti-CD4 was used to mark the Helper-Cell subset of the T-Cells. Thus, in the total lymphocyte population there is a population of cells that contain neither CD3 nor CD4 (i.e., CD3 and CD4 negative, shown in the lower left population of the 2-dimensional scatter plot in FIG. 7), a subset of complex 1-labeled CD3-positive cells that do not have a Phycoerythrin signal (i.e., CD3 positive and CD4 negative, shown in the upper left population of FIG. 7), and a third subset consisting of complex 1 labeled cells that are Phycoerythrin stained (i.e., CD3 and CD4 positive, shown in the upper right population of FIG. 7). It is clear that complex 1 gave base-line separation of the positive and negative cell populations, and that there was no spill over of complex 1 fluorescence into the Phycoerythrin channel. The complex 1 fluorochrome gave a three time brighter signal when the fluorochrome was excited at 514 nm.

The method of synthesizing complex 1 is described in the example below.

EXAMPLE 2

Purification of Dyes: Purification of the fluorochromes was performed on a Spectra-Physica model SP8700 analytical HPLC unit equipped with a C8-RP column. Purification could also be achieved by conventional or flash column chromatography on commercially available C18-RP powder. Water-methanol mixtures were used for elution in all experiments. Dyes were recovered from the fractions with a rotary evaporator at 60–70° C. without appreciable loss. The fluorochrome was passed with unknown counterion composition through a Dowex-50W hydrogen, strongly acidic cation exchange column that had been previously washed with 0.1N sulfuric acid and then distilled water for further purification.

Spectroscopic Measurements and Analytical Determinations: Ultraviolet-visible spectra were measured with a Hewlett-Packard HP 8452 diode array spectrophotometer. The proton NMR spectra were obtained with an IBM 300 FT-NMR spectrometer using $D_2O$ or DMSO $d_6$ as solvent. Fluorescence measurements were performed by using a SPEX Fluorolog 2 system. Quantum yields were determined by well known techniques as previously described in Mujumdar, R. B. et al., "Cyanine Dye Labeling Reagents Containing Isothiocyanate Groups," Cytometry, vol.10, pp.11–19 (1989). NMR signals are described in δ by use of s for singlet, d for doublet, t for triplet, q for quartet, and m for multiplet.

Cell preparation and flow cytometry: Mononuclear leukocytes were obtained by Histopaque density 1.077 separation of peripheral blood from healthy volunteers. The lymphocyte population was selected by flow cytometry based on forward and side scatter characteristics. Subpopulations were identified using specific monoclonal antibodies (CD4, staining T-helper cells and CD3, pan T-cell population). Optimal concentration of complex 1 tagged antibody was determined by analyzing the results of a dilution series. Direct immunofluorescence was accomplished by incubating the recommended amount of labeled antibody with $1-2\times10^6$ cells for 45 minutes at 4° C. Samples were then washed twice in Hank's balanced salt solution (HBSS) containing 2% fetal bovine serum and 0.1% sodium azide. After the final wash, the cells were resuspended in 1 mL of HBSS containing 1% paraformaldehyde and analyzed within one week. Flow cytometry measurements were made with a Becton Dickinson FACS 440 dual laser flow cytometer equipped with a Consort 40 data analysis system. The argon ion laser provided 400 mW of excitation at 488 nm. Fluorescence signals from complex 1 and R-Phycoerythrin were collected using 670/13.5 nm and 575/26 nm band pass filters, respectively.

Calculation of donor quenching efficiency (DQE): Absorption and fluorescence spectra of the donor (alone) and the fluorescent labeling complex were obtained in order to determine the relative concentrations of each in fluorescence experiments. Donor excitation was used to obtain emission spectra of both compounds. DQE was then calculated using $$DQE\% = (1 - F^{ET}A/F\,A^{ET}) \times 100\%$$

where F is the fluorescence intensity of the donor alone, $F^{ET}$ is the intensity of the donor of the complex, A is absorbance at the wavelength of excitation (488 nm) of the donor alone and $A^{ET}$ is the absorbance at the wavelength of excitation (488 nm) of the fluorescent labeling complex.

Syntheses of fluorochromes: Amino-cyanines (CY3NH$_2$, CY3(NH$_2$)$_2$ & CY3NH$_2$SO$_3$) and carboxyalkyl cyanines (CY5COOH, CY3O(SO$_3$)$_2$, CY5 (SO$_3$)$_2$ & CY7 (SO$_3$)$_2$) required as precursors for energy transfer fluorochromes were synthesized by the methods previously described in Ernst, L. A. et al., "Cyanine Dye Labeling Reagents For Sulfhydryl Groups", Cytometry, vol.10, pp.3–10 (1989), Hammer, F. M., THE CYANINE DYES AND RELATED COMPOUNDS, (Wiley pub. New York, 1964), Mujumdar, R. B. et al., "Cyanine Dye Labeling Reagents Containing Isothiocyanate Groups," Cytometry, vol.10, pp. 11–19 (1989), Mujumdar, R. B. et al. "Cyanine dye labeling reagents. Sulfoindocyanine succininmidyl ester," Bioconjugate Chemistry, vol.4, pp.105–111 (1993), and Southwick, P. L. et al., "Cyanine Dye Labeling Reagents: Carboxymethy lindocyanine succinimidyl esters," Cytometry, vol.11, pp.418–430 (1990). The synthesis and properties of one amino-cyanine fluorochrome, CY3NH$_2$SO$_3$, and its conjugation with the succinimidyl ester of CY5(SO$_3$)$_2$ to form complex 1 is described below. The spectral properties for all the fluorochromes are shown in Tables 3 and 4 above. The unsymmetrical trimethinecarbocyanine, CY3—NH$_2$SO$_3$, was synthesized in four steps. Refer to Table 5 below for the structures (I)–(VI).

TABLE 5

| | $R_1$ | $R_2$ | X |
|---|---|---|---|
| I | H | H | Br$^-$ |
| II | CH$_2$Phth | H | Br$^-$ |
| III | CH$_2$Phth | (CH$_2$)$_5$COOH | Br$^-$ |
| IV | SO$_3^-$ | (CH$_2$)$_5$COOH | — |

V, $R_1$ = SO$_3^-$, $R_2$ = CH$_2$Phth
VI, $R_1$ = SO$_3^-$, $R_2$ = CH$_2$NH$_2$ (CY3NH$_2$SO$_3$)

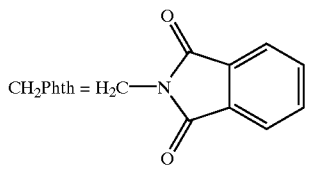

CH$_2$Phth = H$_2$C—

1. Synthesis of 5-Phthalimidomethyl-1-(ε-carboxypentynyl)-2,3,3-trimethylindole, (III). 5-Phthalimidomethyl-2,3,3-trimethylindolenine (II) was synthesized according to the procedure of Gale and Wilshire, "The amidomethylation and bromination of Fisher's base. The preparation of some new polymethine dyes," Aust. J. Chem., vol.30, pp.689–694 (1977). Powdered N-hydroxymethylphthalimide (70 g, 0.4 mol) was added in small portion over a period of 45 min. to a stirred solution of 2,3,3-trimethyl-(3H)-indolenine (I), (70 g, 0.44 mol) in concentrated sulfuric acid (360 mL) at room temperature. The solution was stirred for 70 h at room temperature before being poured onto ice-water. Basification of the solution with conc. ammonium hydroxide gave a yellow powder which was filtered and dried. (111 g, yield 80%, m.p. 180–182° C.). $^1$H NMR (DMSO d$_6$), δ, 7.8–7.95 (m, 4H, phthalimido), 7.4 (s, 1H, 4-H), 7.38 (d, 1H, J=9.0 Hz, 6-H), 7.2 (d, 1H, J=9 Hz, 7-H), 4.7 (s, 2H, —CH$_2$), 2.2 (s, 3H, CH3), 1.2 (s, 6H —(CH$_3$)$_2$).

This dry powder (10 g, 0.3 mol) and 6-bromohexanoic acid (9.1 g, 0.05 mol) were mixed in 1,2-dichlorobenzene (25 mL) and heated at 125° C.) for 12 h under nitrogen. The mixture was cooled, 1,2-dichlorobenzene was decanted and the solid mass was triturated with isopropanol until free powder was obtained. (11 g, yield 80%, m.p. 124–126° C.). $^1$H NMR (DMSO d6), δ, 7.8–7.95 (m, 4H, phthalimido), 7.4 (s, 1H, 4-H), 7.38 (d, 1H, J=9.0 Hz, 6-H), 7.2 (d, 1H, J=9 Hz, 7-H), 4.7 (s, 2H, —CH$_2$), 4.5 (t, 2H, J=7.5 Hz, α —CH$_2$), 2.3 (t, 2H, J=7 Hz, ε-CH$_2$), 1.99 (m, 2H, β-CH$_2$), 2.3–1.7 (m, 4H, γ-CH$_2$ and δ-CH$_2$ merged with s of 6H-(CH$_3$)$_2$).

2. Synthesis of 1-(ε-Carboxypentynyl)-2,3,3-trimethylindoleninium-5-sulfonate (IV). Compound (IV) was synthesized according to the procedure described previously by Mujumdar, R. B. et al., Bioconjugate Chemistry, (1993), supra. The potassium salt of 2,3,3-trimethylindoleninium-t-sulfonate (11 g, 0.04 mol) and 6-bromohexanoic acid (9.8 g, 0.05 mol) were mixed in 1,2 dichlorobenzene (100 mL) and heated at 110° C. for 12 h under nitrogen. The mixture was cooled. 1,2-dichlorobenzene was decanted and the solid mass was triturated with isopropanol until free powder was obtained, (11 g, yield 80%) λmax (water) 275 nm: $^1$H NMR (D$_2$O) δ8.13 (s, 1H, 4-H), 8.03 (dd. 1H, J=9.0, 1.1 Hz, 6-H), 7.2 (d, 1H, J=9.0 Hz, 7-H), 4.51 (t, 2H, J=7.5 Hz, α-CH$_2$), 2.25 (t, 2H, J=7.5 Hz, γ-CH2$_2$), 1.99 (m, 2H, β-CH2-), 1.35–1.66 (m, 4H, δ-CH$_2$, γ-CH$_2$), 1.61 (s, 6H, —(CH$_3$)$_2$). R$_f$=0.55 (C-18, water-methanol, 25%).

3. Synthesis of Intermediate: A solution of 1-(γ-carboxypentynyl)-2,3,3-trimethylindoleninium-5-sulfonate (IV) (10 g, 0.03 mol) and N, N' diphenylformamidine (7.2 g, 0.04 mol) in acetic acid (20 mL) was heated to reflux for 1 h. Acetic acid was removed on a rotary evaporator and the product washed with ethyl acetate (3×50 mL) whereupon a dark brown solid was obtained. λmax (water) 415 nm, R$_f$=0.32 (C18, 25% methanol in water). The crude product thus obtained was used for the next reaction without further purification. The solid (3.8 g) was dissolved in a mixture of acetic anhydride (10 mL) and, pyridine (5 mL). 5-Phthalimidomethyl-1-(ε-carboxypentynyl)-2,3,3-trimethylindole, (III)(2.6 g, 6 mmol) was added and the reaction mixture was heated at 110° C. for 1 h. The solution was cooled and diluted with several volumes of diethyl ether (500 mL). Product separated in the form of red powder from which supernatant fluid was removed by decantation. It was dissolved in a minimum volume of methanol and reprecipitated with 2-propanol. The product was collected on a filter paper and dried to yield 5.3 g of compound (V). It was purified by flash column chromatography on reverse-phase C18 using a water-methanol mixture as eluent, (1.6 g, yield 30%). λmax (water) 554 nm, ε1.3×10$^5$ L/mol-cm. $^1$H NMR (CD$_3$OD) δ8.5 (t, 1H, J=14 Hz, β-proton of the bridge); 7.8–8.0 (m, 6H, 4 protons of phthalimido group & 4-H & 6-H of sulfoindole ring), 7.55 (s, 2H, 4'-H); 7.6 (d, 1H, J=12 Hz, 6'-H); 7.3 (two d. 2H, 7-H & 7'-H); 6.1–6.3 (t, 2H, α α' protons of the bridge); 4.1 (m, 4H. α & α' —CH$_2$—); 2.9 (t, 2H, J=7 Hz, —CH$_2$COOH); 1.4–2.0 (m, 21H, three —CH$_2$, one —CH$_3$ and two —(CH$_3$)$_2$), methyl protons of the methylphthalimido group are merged in a water signal at 4.8.

4. Hydrolysis of (V) to Give (VI). (1 g. 1.1 mmol) was dissolved in concentrated hydrochloric acid (5 mL) and heated under reflux for 12 h. After cooling, the crystalline phthalic acid was filtered off. The filtrate was concentrated with a rotary evaporator and then slowly neutralized with concentrated ammonium hydroxide while the temperature was kept below 30° C. Pure fluorochrome CY3NH$_2$SO$_3$ (VI) was obtained by reverse phase (C18) column chromatography using a water-methanol mixture as eluent. λmax (methanol) 552 nm, $^1$H NMR (DMSO, d$_6$) δ8.45 (t, J=7.2 Hz, 1H, 9-H); 7.3–7.9 (m, 6H, aromatic protons); 6.55 (dd, 2H, 8 & 8–H); 4.5 (m, 4H, N—CH$_2$); 4.1 (s, 2H, C$\underline{H}_2$NH$_2$); 2.15 (t, 2H, CH$_2$COOH); 1.25–1.8 (broad m, 24H, 2-(CH$_2$)2 & 6-C—(CH$_3$)$_2$). R$_f$ 0.415 (RP C18 60% methanol in water)

Figure 5:
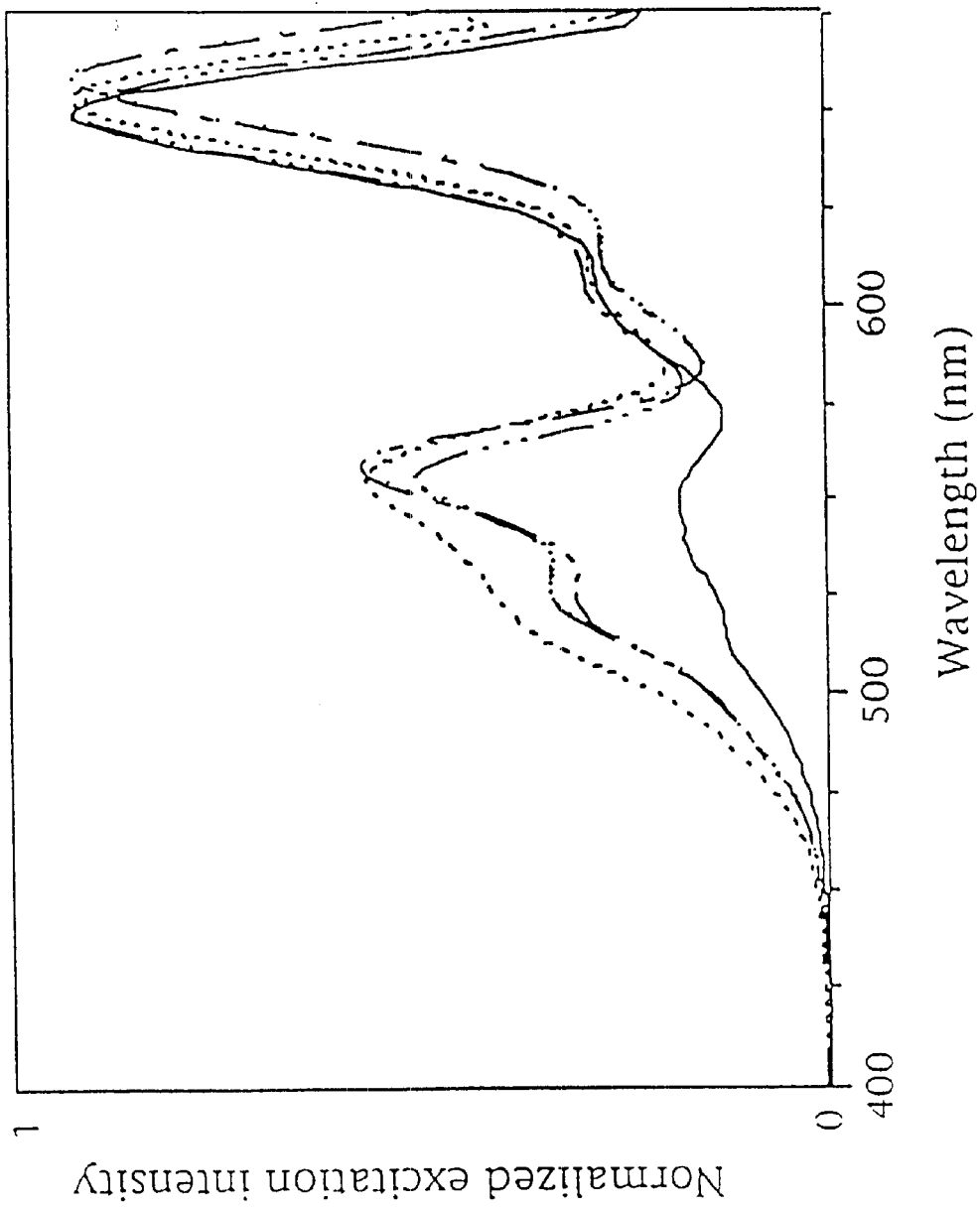
FIG. 5 illustrates a normalized excited spectra of the complex 1 in PBS (solid line), methanol ( ), glycerol ( ), and complex 1-streptavidin conjugate in PBS (----)

5. Synthesis of complex 1. Dry powder of CY5(SO$_3$)$_2$ succinimidylester (425 mg, 0.26 mmol) was added in small portions to a well stirred solution of CY3NH$_2$SO$_3$ (200 mg, 0.26 mmoles) in 10 mL of carbonate-bicarbonate buffer (0.1M, pH 9.4). Stirring was continued for additional 30 minutes after which the reaction mixture was purified by flash column chromatography on C18 reverse phase powder using water:methanol (6.3:3.7) as solvent as eluent. 5 mL fractions were collected and monitored by TLC. Fractions containing CY5(SO$_3$)$_2$ acid and CY3NH$_2$SO$_3$ were discarded. Violet colored fractions were checked by ultraviolet light in methanol and the fractions containing complex 1 fluorochrome (FIG. 3) were pooled. Evaporation of the solvent yielded 150 mg of complex 1 as violet powder (37%) R$_f$=0.45 (RP 37% methanol in water) fluorochrome 1:1 yield 7. Reaction of Succinimidyl Ester with Antibody and streptavidin. A stock solution of the complex 1 fluorochrome succinimidyl active ester was made in dry DMF (1 mg/100 mL). In one sample, one milligram Sheep γ-globulin was dissolved in 0.25 mL carbonate/bicarbonate buffer (approximately 6.45 mmol/0.25 mL). In another, streptavidin was dissolved in 0.25 mL of the carbonate/bicarbonate buffer. Appropriate volumes of the fluorochrome stock were added to 0.25 mL portions of each protein solution to produce desired starting fluorochrome to antibody ratios, and each reaction mixture was stirred at room temperature for 30 minutes. The protein conjugate was separated from unreacted fluorochrome in each sample by gel filtration chromatography over sephadex G-50 (0.7×20 cm column), using PBS, pH 7.4, containing 0.1% azide. Dye conjugated proteins eluted as colored bands well separated from the unreacted fluorochrome. The normalized spectrum of the complex 1-streptavidin conjugage in PBS is shown in FIG. 5. The absorbance spectrum of complex 1-Sheep IgG in PBS is shown in FIG. 6. FIG. 7 shows the flow cytometry analysis of complex 1-streptavidin used to detect CD3 antibody.

EXAMPLE 3

Several other complexes were synthesized.

Figure 8:
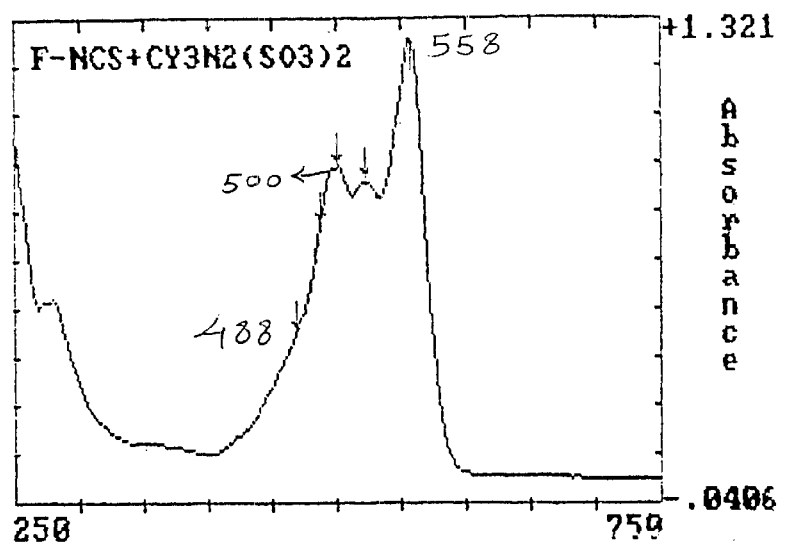
FIG. 8 is the absorbance spectrum for the complex consisting of fluorescein and a trimethine cyanine.
Figure 9:
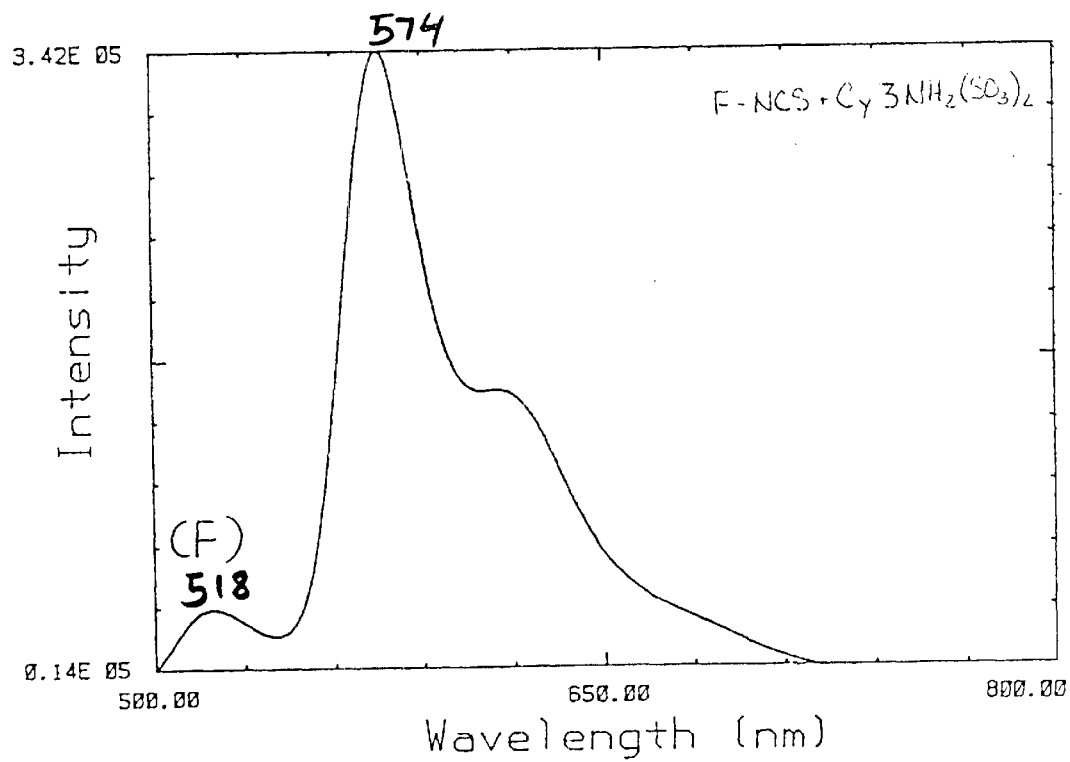
FIG. 9 is the fluorescence spectrum for the complex of FIG. 8.

FIGS. 8 and 9 shown the absorbance and emission spectra, respectively, for the complex fluorescein-CY3NH$_2$SO$_3$ in methanol having the structure.

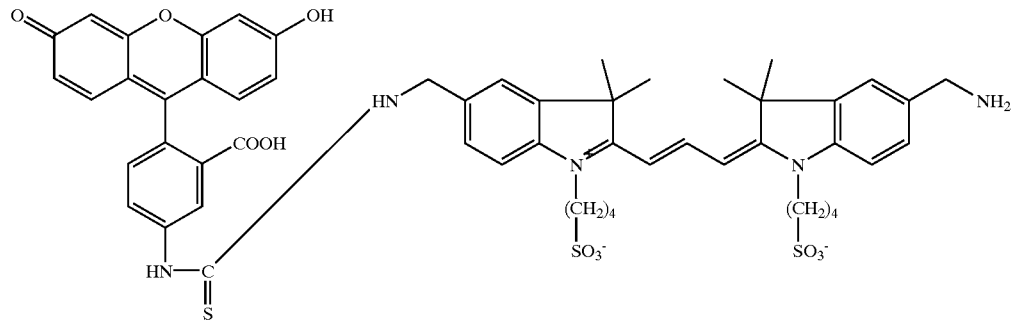

37%. $^1$H NMR spectrum recorded in D$_2$O showed broad signals and were difficult to assign. The fluorochrome was purified on a strongly acidic ion-exchange column (Dowex 50) to remove cationic counter ions. High resolution FAB mass spectrometry showed (M+H)+ion at 1391.83 (C$_{73}$H$_{91}$N$_5$O$_{16}$S$_3$+H requires 1391.73).

6. Succinimidyl Ester of Energy Transfer Cyanine Dye Complex 1 (60 mg, 0.04 mmol) was dissolved in a mixture of dry DMF (1 mL), and dry pyridine (0.05 mL). Disuccinimidyl carbonate (DSC) (46 mg, 0.18 mmol 1.5 equiv/ carboxyl group was added and the mixture was stirred at 55–60° C. for 90 min. Under nitrogen. After diluting the mixture with dry diethyl ether (20 mL), the supernatant was decanted. The product was washed repeatedly with ether, filtered and dried under vacuum. The formation of the active succinimidyl ester was confirmed by its reaction with benzylamine in DMF or its reaction with taurine in a pH 9.4 bicarbonate buffer. Reversed phase C18 TLC spotted with the conjugate, the succinimidyl ester and hydrolyzed carboxylate product for comparison was developed with water-methanol (1:1) mixture. R$_f$=0.78 (Acid), 0.3 (Benzylamine adduct).

Figure 10:
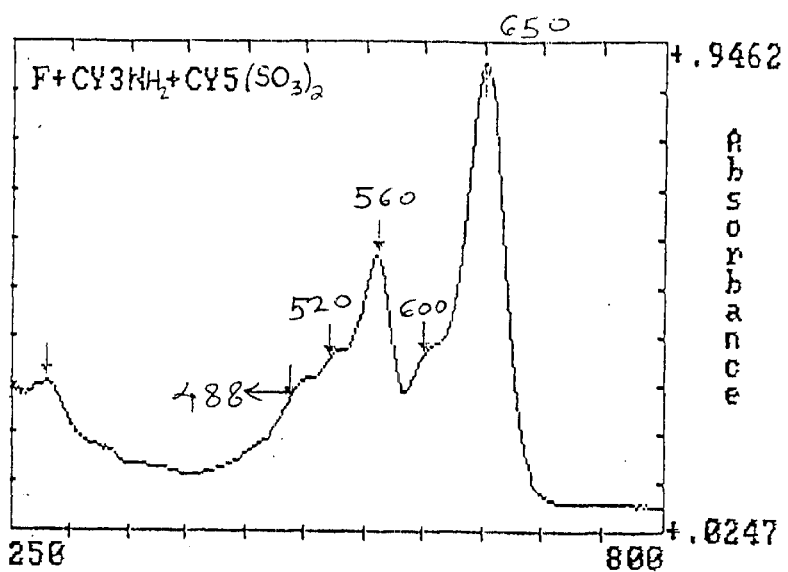
FIG. 10 is the absorbance spectrum for the complex consisting of fluorescein, a trimethine cyanine and a pentamethine cyanine.
Figure 11:
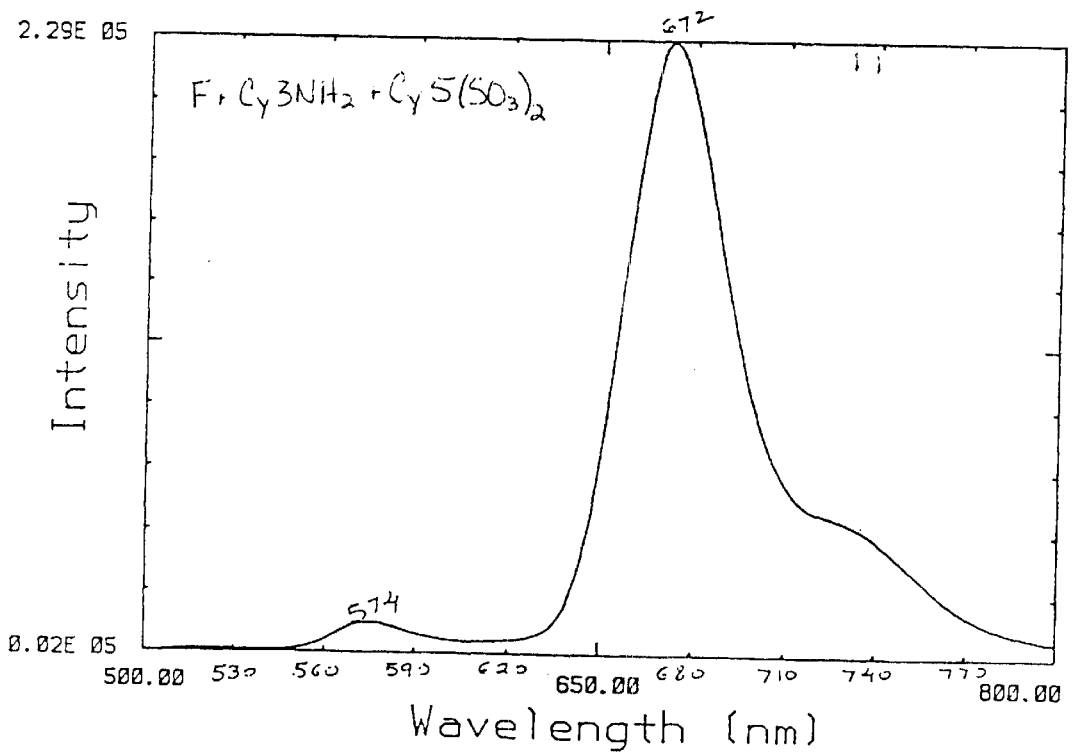
FIG. 11 is the fluorescence spectrum for the complex of FIG. 10.
Figure 12:
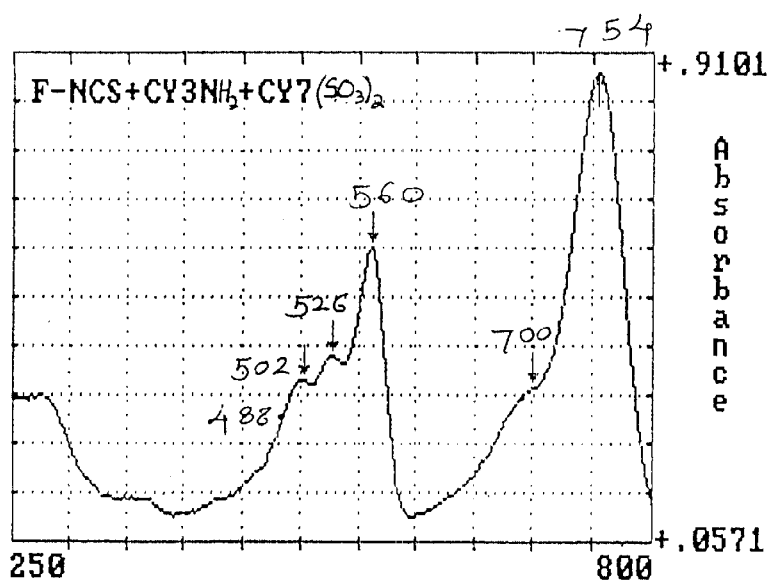
FIG. 12 is the absorbance spectrum for the complex consisting of fluorescein, a trimethine cyanine and a heptamethine cyanine; and, FIG. 13 is the fluorescence spectrum for the complex of FIG. 12.
Figure 13:
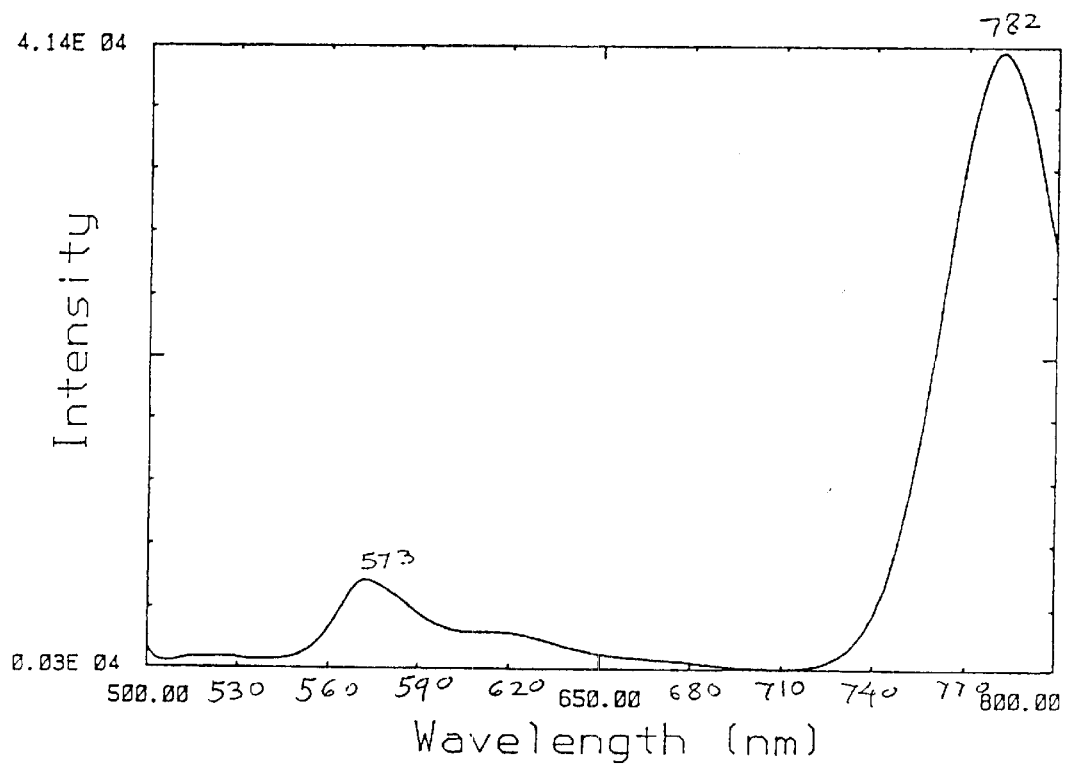

Excitation was at 488 nm with fluorescence emission at 574 nm. The quantum yield was 0.041, the Stokes shift was 74 and the % efficiency of the energy transfer was 98.3%. The absorbance max. for each of the fluorochromes in the complex is 500 and 558. FIGS. 10 and 11 shown the absorbance and emission spectra, respectively, for the complex fluorescein-CY3(NH$_2$)$_2$—CY5(SO$_3$)$_2$ in methanol. The absorbance max. for each of the fluorochromes is 500, 560 and 650. Excitation was at 488 nm and emission at 672 nm. The quantum yield was 0.1566, Stokes shift was 172 and the % efficiency of the energy transfer was 99%. FIGS. 12 and 13 shown the absorbance and emission spectra, respectively, for the complex fluorescein-CY3(NH$_2$)$_2$—CY7 (SO$_3$)$_2$. The absorbance max. for each fluorochrome is 500, 560 and 754. Excitation was as 488 nm and emission at 782 nm. The Stokes shift was 282 and the % efficiency was 99%. These series of spectra demonstrate the efficient energy transfer with long Stokes shifts. Each emission spectrum shows substantially all of the emission coming from the final acceptor fluorochrome in each series with only minimal emission from either the donor fluorescein in FIG. 9 or the intermediate cyanine in FIGS. 11 and 13.

Multiparameter analyses can be done of multiple samples to detect the presence of target biological compounds. Each sample is labeled by well known labeling methods with a different complex. For example, one sample suspected of containing a target biological compound is incubated with a single fluorochrome, such as fluorescein, cascade blue, a BODIPY dye or one of the monomethine rigidized dyes or CY30 $(SO_3)_2$ or CY3 $(SO_3)_2$, all emitting in the 500–575 nm wavelength range (green to orange). A second sample suspected of containing the target biological compound (the same compound or a different compound as that in sample 1), is incubated with a complex of the invention, for example fluorescein-CY3NH$_2$ which will absorb light at 488 nm and emits fluorescence at 574 nm (orange). Additional samples suspected of containing another target compound are incubated with other labeling complexes of the invention, such as fluorescein-CY3-CY5 and fluorescein-CY3-CY7 both of which absorb light at 488 nm, but emit fluorescence at 672 nm and 782 nm, respectively (red to deep red). After a suitable period to permit the fluorescent labels to bind with the target compounds, unbound label is washed and the labeled samples are mixed. Detection is possible with a single wavelength excitation source, i.e., at laser line 488 nm. Each differently labeled sample will fluoresce a different color at the emission wavelength of its particular label. Those skilled in the art will recognize that the fluorescent labeling complexes of the present inventor can be used for a variety of immunofluorescent techniques, including direct and indirect immunoassays, or, competitive immunoassays and other known fluorescence detection methods. The conditions of each incubation, e.g., pH, temperature and time are known in the art, but generally room temperature is preferred. If reacting with a amine, pH 9.4 is preferred. The pH is adjusted depending on the optimum reaction conditions for the particular reactive groups according to known techniques.

The fluorescent labeling complexes may be used to form reagents by covalently binding the complexes to a carrier material, such as polymer particles, cells, glass beads, antibodies, proteins, enzymes and nucleotides or nucleic acids (DNA and RNA) and analogs thereof which have been derivatized to include at least one first reactive group capable of forming a covalent bond with the functional group on the labeling complex (or a functional group capable of forming a covalent bond with a reactive group on the complex, as described above) and at least one second reactive group (or functional group, as the case may be) having specificity for, and being capable of forming a covalent bond with, a target biological compound, such as antibodies, cells, drugs, antigens, bacteria, viruses and other microorganisms. When the carrier has functional groups, it may be antibody or DNA suited for attachment to antigen or a complementary DNA sequence, respectively. When the carrier material has reactive groups on it, the carrier may be a polymer particle or an antigen suitable for attachment to DNA or an antibody, for example. Techniques for covalently binding fluorochromes to carrier molecules such as those mentioned are well known in the art and readily available in the literature. The carrier material can further include nucleotide derivatized to contain one of an amino, sulfhydryl, carboxyl, carbonyl or hydroxyl groups, and oxy or deoxy polynucleic acids derivatized to contain one of an amino, sulfhydryl, carboxyl, carbonyl or hydroxyl groups. The functional groups on the carrier material which are complementary to, i.e., form covalent bonds with, the reactive groups of the labeling complexes of the invention include amino, sulfhydryl, carboxyl, hydroxyl and carbonyl groups.

A comparison of the energy transfer complex of the present invention to the conventional R-Phycoerythrin dyes is shown in Table 6 below.

TABLE 6

COMPLEX 2 vs R-PHYCOERYTHRIN

| | R-Phycoervthrin | Complex 2 |
|---|---|---|
| Excitation wavelength | 488 | 488 |
| Emission wavelength | 580 | 578 |
| 488-laserline Flow-Cytometer | PE fluorescence was greatly reduced at pH 8.5 & extinguished at pH 9.5 | signals were stable throughout pH range |
| MW | 240000 | 1667 |
| Staining | do not penetrate readily into intracellular tissues to reach target antigen | labeled Ab penetrates into intracellular tissues to reach target antigen |
| Binding Rate | rate of binding to antigen is slow | rapid binding |

The energy transfer complexes of the present invention provide a valuable set of fluorescent labels which are particularly useful for multiparameter analysis and importantly, are sufficiently low in molecular weight to permit materials labeled with the fluorescent complexes to penetrate all structures. As such, the complexes are well suited for use as DNA probes. The complexes of the invention and the reagents that can be made from them offer a wide variety of fluorescent labels with large Stokes shifts. Those in the art will recognize that the complexes of the invention can be used in a variety of fluorescence applications over a wide range of the visible spectrum.

What we claim is:

1. A set of fluorescent labeling complexes each of said complexes comprising:

i) a first fluorochrome having first absorption and emission spectra;

ii) a second fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome, the first and second fluorochromes being selected from the cyanine dyes, fluoresceins, rhodamines, pyrene trisulphonates and derivatives of the bispyrromethine boron difluoride dyes;

iii) at least one linker group having between 2 and 20 bond lengths for covalently attaching said first and second fluorochromes for transfer of resonance energy between said first and second fluorochromes;

iv) at least one target bonding group capable of forming a covalent bond with a target compound wherein the target bonding group is a reactive group for reacting with a functional group on the target material;

wherein the combined molecular weight of said first and second fluorochromes and said linker group in each of said complexes is less than 20,000 Daltons, wherein at least two complexes of said set absorb at the same wavelength and emit (fluoresces) at significantly different emission wavelengths, and wherein at least one of said first or second fluorochromes in each of said complexes is a cyanine dye.

2. A set according to claim 1 wherein each of said complexes further comprises water solubilizing constituents attached thereto, said water solubilizing constituents being unreactive with said target bonding group.

3. A set according to claim 2 wherein said water solubilizing constituents are selected from the group consisting of amide, sulphonate, sulphate, phosphate, quaternary ammonium, hydroxyl, guanidinium and phosphonate.

4. A set according to claim 1 wherein said target bonding group in each of said complexes is a reactive group selected from the group consisting of succinimidyl ester, isothiocyanate, isocyanate, haloacetamide, dichlorotriazine, maleimide, sulphonyl halide, alkylimidoester, arylimidoester, substituted hydrazine, substituted hydroxylamine, carbodiimide, acyl halide, anhydride, phosphoramidite, acrylate and acrylamide.

5. A set according to claim 1 wherein the combined molecular weight of said first and second fluorochromes and said linker group in each of said complexes is within the range of 500 to 10,000 Daltons.

6. A set according to claim 1 wherein one or more of said fluorescent labeling complexes further comprises a third fluorochrome having third absorption and emission spectra covalently attached to said second fluorochrome; the wavelength of the emission maximum of said third fluorochrome being longer than the wavelength of the emission maximum of said second fluorochrome and a portion of the emission spectrum of said second fluorochrome overlapping a portion of the absorption spectrum of said third fluorochrome such that excitation of said first fluorochrome produces fluorescence from said third fluorochrome.

7. A set according to claim 6 wherein one or more of said fluorescent labeling complexes further comprise water solubilizing constituents attached thereto, said water solubilizing constituents being unreactive with said target bonding groups on each of said complexes.

8. A set according to claim 6 wherein said first fluorochromes are selected from the group consisting of monomethine rigidized cyanine dyes, a trimethine cyanine dye, fluorescein, pyrene trisulphonate, bispyrromethine boron difluoride dyes and said second and third fluorochromes are polymethine cyanine dyes.

9. A set of fluorescent labeling complexes each of said complexes comprising:
  i) a first fluorochrome having first absorption and emission spectra;
  ii) a second fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome;
  iii) at least one linker group chosen from the group consisting of alkyl chains containing from 1 to 15 carbon atoms, which may optionally include oxygen atoms as ether linkages, or nitrogen atoms as amine linkages, or CONH groups as amide linkages, for covalently attaching said first and second fluorochromes for transfer of resonance energy between said first and second fluorochomes;
  iv) at least one target bonding group capable of forming a covalent bond with a target compound;
wherein at least one of said first or second fluorochromes in each of said complexes is a cyanine dye and wherein the combined molecular weight of said first and second fluorochromes and said linker group in each of said complexes is less than 20,000 Daltons.

10. A set of reagents each reagent comprising:
  A) a fluorescent water soluble labeling complex comprised of:
    i) one or more low molecular weight first fluorochromes, each having first absorption and emission spectra, covalently attached through a linker group to one or more low molecular weight second fluorochromes, each having second absorption and emission spectra, and wherein the wavelength of the emission maximum of at least one said second fluorochrome is longer than the wavelength of the emission maximum of at least one said first fluorochrome and a portion of the absorption spectrum of at least one said second fluorochrome overlaps a portion of the emission spectrum of at least one said first fluorochrome for transfer of energy absorbed by said first fluorochrome upon excitation with light to said second fluorochrome;
    ii) at least one target bonding group capable of forming a covalent bond with a carrier material; and,
    iii) at least one water solubilizing constituent attached to said complex, said water solubilizing constituent being unreactive with said at least one target bonding group;
  wherein at least one of said first or second fluorochromes is a cyanine dye and the linker group is chosen from the group consisting of alkyl chains containing from 1 to 15 carbon atoms, which may optionally include oxygen atoms as ether linkages, or nitrogen atoms as amine linkages, or CO—NH groups as amide linkages;
  B) a carrier material having a group that reacts with said target bonding group of said complex and is covalently bound thereto.

11. A set according to claim 10 wherein said first fluorochrome is selected from the group consisting of monomethine rigidized cyanine dyes, a trimethine cyanine dye, fluorescein, pyrene trisulphonate, bispyrromethine boron difluoride dyes and said second fluorochrome is a polymethine cyanine dye.

12. A set according to claim 10 wherein said carrier material has a functional group selected from the group consisting of amino, sulphydryl, carbonyl, hydroxyl and carboxyl, phosphate and thiophosphate and said carrier material is selected from the group consisting of antibody, lipid, protein, carbohydrate, nucleotide derivatized to contain one of an amino, sulphydryl, carbonyl, hydroxyl and carboxyl, phosphate and thiophosphate groups and oxy or deoxy polynucleic acids derivatized to contain one of an amino, sulphydryl, carbonyl, hydroxyl and carboxyl, phosphate and thiophosphate groups.

13. A method of labeling a carrier material with one of a set of fluorescent labeling complexes, comprising incubating an aqueous sample containing a carrier material with a low molecular weight, water soluble fluorescent labeling complex comprised of:
  i) a first fluorochrome having first absorption and emission spectra covalently linked through a linker group to a second fluorochrome having second absorption and emission spectra, the wavelength of the emission maximum of said second fluorochrome being longer than the wavelength of the emission maximum of said first fluorochrome, and the absorption spectrum of said second fluorochrome overlapping the emission spectrum of said first fluorochrome for transfer of energy absorbed by said first fluorochrome upon excitation with light to said second fluorochrome, wherein at least one of said first or second fluorochromes in said complex is a cyanine dye;

ii) a target bonding group attached to said complex capable of forming a covalent bond with a complementary group of said carrier material, and iii) water solubilizing constituents attached to said complex for conferring a polar characteristic to said complex, said water solubilizing constituents being unreactive with said bonding group;

for a period of time sufficient for covalently binding said bonding group of said complex to said complementary group of said carrier material.

14. Use of a set of fluorescent labeling complexes for analysis or detection comprising incubating a fluorescent labeling complex of said set with at least one target material, each of said fluorescent labeling complexes comprising:

i) a first fluorochrome having first absorption and emission spectra;

ii) a second fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome, the first and second fluorochromes being selected from the cyanine dyes, fluoresceins, rhodamines, pyrene trisulphonates and derivatives of the bispyrromethine boron difluoride dyes;

iii) at least one linker group having between 2 and 20 bond lengths, which may optionally include oxygen atoms as ether linkages, or nitrogen atoms as amine linkages, or CONH groups as amide linkages, for covalently attaching said first and second fluorochromes for transfer of resonance energy between said first and second fluorochromes;

iv) at least one target bonding group capable of forming a covalent bond with a target compound wherein the target bonding group is a reactive group for reacting with a functional group on the target material;

wherein the combined molecular weight of said first and second fluorochromes and said linker group in each of said complexes is less than 20,000 Daltons, wherein at least one of said first and second fluorochromes in each of said complexes is a cyanine dye, and wherein at least two complexes of said set absorb at the same wavelength and emit (fluoresces) at significantly different emission wavelengths; and measuring and comparing the differences in fluorescent emission between said fluorescent labeling complexes.

15. Use of a set of fluorescent labeling complexes for analysis and detection comprising incubating a fluorescent labeling complex of said set with at least one target material, each of said fluorescent labeling complexes comprising:

i) a first fluorochrome having first absorption and emission spectra;

ii) a second fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome;

iii) at least one linker group chosen from the group consisting of alkyl chains containing from 1 to 15 carbon atoms, which may optionally include oxygen atoms as ether linkages, or nitrogen atoms as amine linkages, or CONH groups as amide linkages, for covalently attaching said first and second fluorochromes for transfer of resonance energy between said first and second fluorochromes;

iv) at least one target bonding group capable of forming a covalent bond with a target compound;

wherein the combined molecular weight of said first and second fluorochromes and said linker group in each of said complexes is less than 20,000 Daltons, and wherein at least one of said first or second fluorochromes in each of said complexes is a cyanine dye; and measuring and comparing the differences in fluorescent emission between said fluorescent labeling complexes.

16. A carrier material or biological compound labeled with one of a set of fluorescent labeling complexes according to claim 1 in which the reactive group of said complex is covalently bound to a functional group on the target material.

17. A carrier material or biological compound covalently labeled with one of a set of fluorescent labeling complexes according to claim 9.

18. A method of labeling a carrier material or target compound by the use of one of a set of fluorescent labeling complexes according to claim 1, said method comprising incubating said complex with the carrier material or target compound under conditions suitable for the formation of a covalent linkage between said complex and said carrier material or target compound.

19. A method according to claim 18 wherein said carrier material or target compound is selected from the group consisting of antibodies, antigens, proteins, carbohydrates, lipids, nucleotides derivatized to contain one of amino, hydroxyl, sulphydryl, carboxyl or carbonyl groups, and oxy or deoxy polynucleic acids derivatized to contain one of amino, hydroxyl, phosphate, thiophosphoryl, sulphydryl, carboxyl or carbonyl groups, cells, polymer particles, or glass beads.

20. A method of labeling a carrier material or target compound by the use of one of a set of fluorescent labeling complexes according to claim 9, said method comprising incubating said complex with the carrier material or target compound under conditions suitable for the formation of a covalent linkage between said complex and said carrier material or target compound.

21. A method according to claim 20 wherein the carrier material or target compound is selected from the group consisting of antibodies, antigens, proteins, carbohydrates, lipids, nucleotides derivatized to contain one of amino, hydroxyl, sulphydryl, carboxyl or carbonyl groups, and oxy or deoxy polynucleic acids derivatized to contain one of amino, hydroxyl, phosphate, thiophosphoryl, sulphydryl, carboxyl or carbonyl groups, cells, polymer particles, or glass beads.

22. A set of reagents comprising fluorescent labeling complexes according to claim 1 each complex absorbing at the same wavelength and emitting at significantly different emission wavelengths, each complex being linked through a covalent bond to a carrier material or target compound selected from the group consisting of antibodies, antigens, proteins, carbohydrates, lipids, nucleotides derivatized to contain one of amino, hydroxyl, sulphydryl, carboxyl or carbonyl groups, and oxy or deoxy polynucleic acids derivatized to contain one of amino, hydroxyl, phosphate, thiophosphoryl, sulphydryl, carboxyl or carbonyl groups, cells, polymer particles, or glass beads.

23. A set of reagents comprising fluorescent labeling complexes according to claim 9 each complex absorbing at the same wavelength and emitting at significantly different emission wavelengths, each complex being linked through a covalent bond to a carrier material or target compound selected from the group consisting of antibodies, antigens, proteins, carbohydrates, lipids, nucleotides derivatized to contain one of amino, hydroxyl, sulphydryl, carboxyl or carbonyl groups, and oxy or deoxy polynucleic acids derivatized to contain one of amino, hydroxyl, phosphate, thiophosphoryl, sulphydryl, carboxyl or carbonyl groups, cells, polymer particles, or glass beads.

24. The method of claim 13, wherein there are different kinds of carrier materials and different kinds of labeling complexes within said set wherein the emission maximum of the second fluorochromes of each different kind of fluorescent labeling complex of said set is different from the at least one other kind of labeling complexes, and said labeling comprises covalently binding one kind of carrier material with one of said set of fluorescent labeling complexes and covalently binding a different kind of said carrier material with a different kind of said set of fluorescent labeling complexes.

25. The method of claim 14, wherein there are first and second carrier materials and wherein said incubating comprises covalently binding said first carrier material with of said set of fluorescent labeling complexes and covalently binding said second carrier material with the another of said set of fluorescent labeling complexes, wherein said set of fluorescent labeling complexes includes complexes that differ from each other in their respective emission wavelengths.

26. The method of claim 15, wherein there are first and second carrier materials and wherein said incubating comprises covalently binding said first carrier material with one of said set of fluorescent labeling complexes and covalently binding said second carrier material with the another of said set of fluorescent labeling complexes, wherein said set of fluorescent labeling complexes includes complexes that differ from each other in their respective emission wavelengths.

27. A set of fluorescent labeling complexes each of said complexes comprising:

i) a first fluorochrome having first absorption and emission spectra;

ii) a second fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome, the first and second fluorochromes being selected from the cyanine dyes, fluoresceins, rhodamines, pyrene trisulphonates and derivatives of the bispyrromethine boron difluoride dyes;

iii) at least one linker group having between 2 and 20 bond lengths for covalently attaching said first and second fluorochromes for transfer of resonance energy between said first and second fluorochromes;

iv) at least one target bonding group capable of forming a covalent bond with a target compound wherein the target bonding group is a reactive group for reacting with a functional group on the target material;

wherein said fluorochromes and said linker in each of said complexes, the relative orientation of the transition moments of the fluorochromes during the excited state lifetime of the first fluorochrome, and the proximity of the fluorochromes, are selected such that there is sufficient energy transfer;

wherein the combined molecular weight of said first and second fluorochromes and said linker group in each of said complexes is less than 20,000 Daltons, wherein at least two complexes of said set absorb at the same wavelength and emit (fluoresces) at significantly different emission wavelengths, and wherein at least one of said first or second fluorochromes in each of said complexes is a cyanine dye.

28. A set of fluorescent labeling complexes each of said complexes comprising:

i) a first fluorochrome having first absorption and emission spectra;

ii) a second fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome, the first and second fluorochromes being selected from the cyanine dyes, fluoresceins, rhodamines, pyrene trisulphonates and derivatives of the bispyrromethine boron difluoride dyes;

iii) at least one linker group having between 2 and 20 bond lengths for covalently attaching said first and second fluorochromes for transfer of resonance energy between said first and second fluorochromes, wherein said linker group optimally orients the transition moments of said first and second fluorochromes;

iv) at least one target bonding group capable of forming a covalent bond with a target compound wherein the target bonding group is a reactive group for reacting with a functional group on the target material;

wherein the combined molecular weight of said first and second fluorochromes and said linker group in each of said complexes is less than 20,000 Daltons, wherein at least two complexes of said set absorb at the same wavelength and emit (fluoresces) at significantly different emission wavelengths, and wherein at least one of said first or second fluorochromes in each of said complexes is a cyanine dye.

29. A set of fluorescent labeling complexes each of said complexes comprising:

i) a first fluorochrome having first absorption and emission spectra;

ii) a second fluorochrome having second absorption and emission spectra, the wavelength of the emission maximum of said second fluorochrome being longer than the wavelength of the emission maximum of said first fluorochrome, and a portion of the absorption spectrum of said second fluorochrome overlapping a portion of the emission spectrum of said first fluorochrome, the first and second fluorochromes being selected from the cyanine dyes, fluoresceins, rhodamines, pyrene trisulphonates and derivatives of the bispyrromethine boron difluoride dyes;

iii) at least one linker group having between 2 and 20 bond lengths for covalently attaching said first and second fluorochromes for transfer of resonance energy between said first and second fluorochromes, wherein said linker group is rigid;

iv) at least one target bonding group capable of forming a covalent bond with a target compound wherein the target bonding group is a reactive group for reacting with a functional group on the target material;

wherein the combined molecular weight of said first and second fluorochromes and said linker group in each of said complexes is less than 20,000 Daltons, wherein at least two complexes of said set absorb at the same wavelength and emit (fluoresces) at significantly different emission wavelengths, and wherein at least one of said first or second fluorochromes in each of said complexes is a cyanine dye.

* * * * *

UNITED STATES PATENT AND TRADEMARK OFFICE
CERTIFICATE OF CORRECTION

PATENT NO.   : 6,479,303 B1                                         Page 1 of 1
DATED        : November 12, 2002
INVENTOR(S)  : Alan Waggoner, Swati R. Mujumdar and Ratnakar B. Mujumdar It is certified that error appears in the above-identified patent and that said Letters Patent is hereby corrected as shown below:

Column 3,
Lines 5 and 6, delete the semi-colon before "20,000 and Daltons" and substitute therefore -- 20,000 Daltons; and preferably in the range of 500 to 10,000 Daltons --.

Column 4,
Line 23, place a period after the word "material".

Column 6,
Line 55, delete the "1" after "fluorochromes".
Line 56, place a period after the word "efficient".

Column 17,
Line 28, delete the semi-colon after the word "cyanine".

Column 18,
Line 30, delete "cross-liking" and substitute therefore -- cross-linking --.

Column 20,
Line 54, delete "DOE" and substitute therefore -- DQE --.

Column 25,
Line 27, delete "inventor" and substitute therefore -- invention --.

Signed and Sealed this

Thirtieth Day of December, 2003

JAMES E. ROGAN
*Director of the United States Patent and Trademark Office*